United States Patent [19]

Turner

[11] Patent Number: 5,427,991
[45] Date of Patent: Jun. 27, 1995

[54] POLYIONIC TRANSITION METAL CATALYST COMPOSITION

[75] Inventor: Howard W. Turner, Houston, Tex.

[73] Assignee: Exxon Chemical Patents Inc., Wilmington, Del.

[21] Appl. No.: 31,004

[22] Filed: Mar. 12, 1993

Related U.S. Application Data

[63] Continuation-in-part of Ser. No. 796,729, Nov. 25, 1991, abandoned.

[51] Int. Cl.[6] .............................................. B01J 31/00
[52] U.S. Cl. .................................. 502/103; 502/117; 502/152; 502/155; 502/159; 526/131; 526/160; 526/163
[58] Field of Search ............... 502/103, 117, 152, 155, 502/159

[56] References Cited

U.S. PATENT DOCUMENTS

| | | | |
|---|---|---|---|
| 5,026,798 | 6/1991 | Canich | 526/127 |
| 5,055,438 | 10/1991 | Canich | 502/117 |
| 5,057,475 | 10/1991 | Canich et al. | 502/104 |
| 5,096,867 | 3/1992 | Canich | 502/103 |
| 5,120,867 | 6/1992 | Welborn, Jr. | 556/12 |

FOREIGN PATENT DOCUMENTS

| | | |
|---|---|---|
| 0225867 | 12/1983 | European Pat. Off. . |
| 0129368 | 6/1984 | European Pat. Off. . |
| 0163214 | 5/1985 | European Pat. Off. . |
| 0230247 | 1/1987 | European Pat. Off. . |
| 0277004 | 1/1987 | European Pat. Off. . |
| 0277003 | 1/1988 | European Pat. Off. . |
| 0293815 | 6/1988 | European Pat. Off. . |
| 0416815 | 8/1990 | European Pat. Off. . |
| 0520732 | 6/1992 | European Pat. Off. . |
| WO87/00177 | 1/1987 | WIPO . |
| WO91/09882 | 7/1991 | WIPO . |
| WO92/00333 | 1/1992 | WIPO . |
| WO92/01006 | 1/1992 | WIPO . |
| WO92/12162 | 7/1992 | WIPO . |

Primary Examiner—Asok Pal
Attorney, Agent, or Firm—W. G. Muller

[57] ABSTRACT

Ionically activated metallocene catalyst compositions which are useful in the polymerization of olefins comprise transition metal cationic components associated with and stabilized by a polyanionic moieties constituted of non-coordinating anionic groups chemically bonded to core components. The transition metal cationic components typically are cyclopentadienyl-group containing Group 4, 5, and 6 metal compounds having a hydrolyzable ligand such that they react with the activator compounds so as to form the cationic components in non-coordinating association with bulky, labile anions derived from the activator compound which in turn is chemically bound to the core component, such as a polymeric or metal oxide support.

27 Claims, 8 Drawing Sheets

POLYIONIC TRANSITION METAL CATALYST COMPOSITION

CROSS REFERENCE TO OTHER RELATED APPLICATIONS

This application is a continuation-in-part of U.S. patent application Ser. No. 796,729 filed Nov. 25, 1991, now abandoned.

FIELD OF THE INVENTION

This invention relates to polyionic catalyst compositions and their use to polymerize olefins, diolefins and-/or acetylenically unsaturated monomers to homopolymer and copolymer products.

BACKGROUND OF THE INVENTION

Ziegler-Natta (Z-N) and metallocene-alumoxane type catalyst systems for the polymerization of olefins are well known in the art. Recently a new, ionic pair type of catalyst has been developed which yields polymers of improved properties compared to those made with conventional type catalysts systems. The first, among various publications, to describe this new system was Turner, et al. in EPA 277,003 and 277,004. EPA 277,003 and EPA 277,004 disclose new cyclopentadienyl based catalyst systems comprising an ionic compound wherein the cyclopentadienyl transition metal component or metallocene is reacted with an activator comprising an anion and a cation; the cation being one which is reactable with a non-cyclopentadienyl ligand of the cyclopentadienyl moiety to yield as the reaction product a neutral ligand derivative, and a cationic metallocene species to which the anion of the activator compound is essentially non-coordinating. EPA 277,003 describes an anion component which comprises a plurality of boron atoms while EPA 277,004 describes an anion species which is a single coordination complex having ligand(s) shielding a central charge-bearing metal or metalloid atom.

These ionic complexes can optionally be placed on a support medium in accordance with that described in PCT WO91/09882 or copending, commonly assigned application U.S. Ser. No. 926,006 filed on Aug. 5, 1992. In accordance with WO 91/09882, the ionic catalyst is physisorbed onto an inert carrier which has been previously dehydrated and treated with an alkyl aluminum solution. The ionic catalyst is not covalently bonded onto the support carrier and is extractable or desorble by solvents.

While improvements in catalyst activity, selectivity, and processing were observed with both the homogeneous and heterogeneous ionic catalyst described above, further improvements are sought for the catalyst system through anion effects as well as to address the issue of catalyst desorption found when hetereogeneous catalyst are used.

SUMMARY OF THE INVENTION

This invention relates to new polyanionic non-coordinating anions or activator moieties comprising a plurality of metal or metalloid atom-containing non-coordinating anionic groups pendant from and chemically bonded to a core component, which can be used to prepare a wide variety of new ionic catalysts compositions which are useful in the polymerization of olefins, diolefins and/or acetylenically unsaturated monomers. These non-coordinating anions are stabilized by a sufficent number of cations to balance charge on the composition or catalyst formed. When exposed to unsaturated monomers, the polymerization catalyst of this invention yield a wide variety of homo or copolymers having variable molecular weight, molecular weight distribution and comonomer content.

The invention provides polyanionic non-coordinating anions and methods of preparing such anions. The invention further provides new ionic catalyst compositions and methods of preparing such materials from the polyanions. The polyanionic moiety may exist in combination with balancing cationic species. Thus, another aspect of the invention provides a polyanionic activator composition comprising the defined polyanionic moiety and a plurality of cations which balance the charge of the non-coordinating anionic groups. The invention further provides a method of producing the defined activated catalyst composition which comprises contacting a transition metal compound having at least one leaving group ligand, for example, a ligand which is hydrolyzable with water, and the defined polyanionic activator composition for a time and under conditions sufficient to allow charge balancing cations of the polyanionic activator to react with the leaving group ligands of the transition metal compound.

In one application, the polyanionic activators are used to prepare a catalyst system of enhanced performance by immobilizing the catalyst on a catalyst support material. The heterogeneous, or supported, catalyst of this invention can be used in a wide variety of commercial processes including gas phase, slurry or fixed bed reactors.

The ionic catalyst compositions are prepared by reacting a transition metal catalyst precursor ZX with a polyionic ion-exchange activator compound $[Ct^{c+}]_{y'}[(\text{NCA}^{b-})_y T]^{by-}$ to form a neutral by-product CtX and the active polyionic catalyst system $[Z^{n+}]_{by}[(\text{NCA}^{b-})_y T]^{by-}$, wherein Z is a ligand stabilized transition metal compound, $Ct^{c+}$ is a cation which balances charge and can be designed to react with the leaving group X which is bonded to Z, y' is the number of $Ct^{c+}$ cations, n is the charge on the catalyst cations $[(\text{NCA}^{b-})_y T]^{by-}$ is a polyanionic non-coordinating counter ion comprised of pendent non-coordinating anions (NCA) bonded to T, a core atom, a core molecule, a core polymeric or a core network such as silica (e.g. particles) or metal oxide surface of a metal substra.e, b is the charge on the non-coordinating anion and y is an integer greater than or equal to 2. Similar procedures can be used to generate polyionic catalysts having an active site with a cationic charge greater than 1 ($Z^{n+}$ where n is an integer greater than 1). The preferred ligand stabilized transition metal components include high oxidation state Group IV metal alkyl or hydride complexes having between 0 and 2 covalently-bound cyclopentadienyl ligands.

DETAILED DESCRIPTION OF THE PREFERRED EMBODIMENTS

Figure 1:
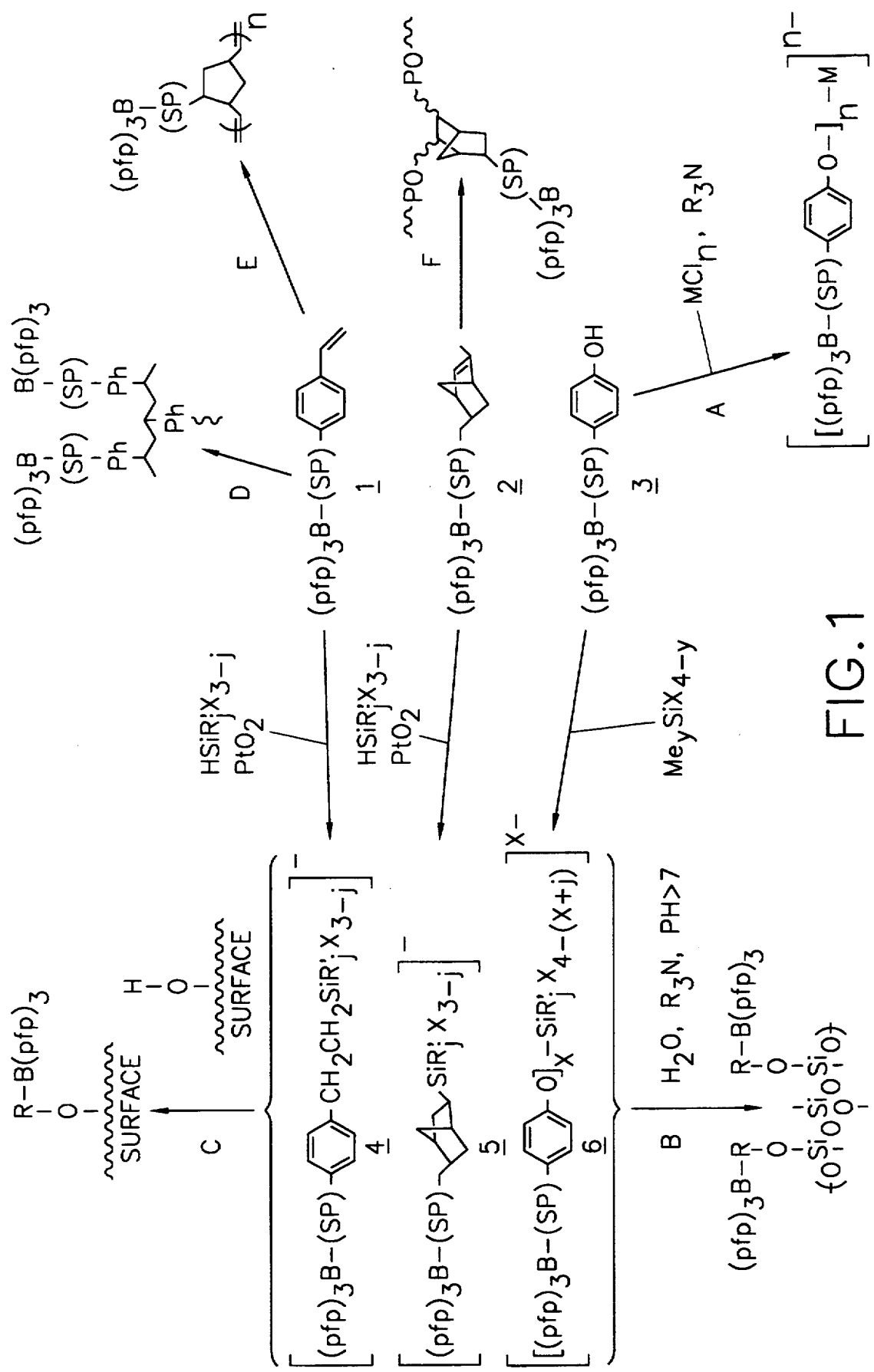
FIG. 1 is a schematic diagram which illustrates three of the most preferred synthons (1,2 and 3) and the manner by which they may be utilized to prepare derivative synthons (4, 5 and 6) and polyionic activator compositions (A-F).

L represents a neutral Lewis basic ligand such as phosphine; diphos is a chelating phosphine; Cp is a substituted or unsubstituted cyclopentadienyl ligand; ACp represents two substituted or unsubstituted cyclopentadienyl ligands which may be bridged or unbridged, and may be the same or different; and R represents a hydrocarbyl substituent.

Discrete catalyst cations having a variety of end uses are well known in the art. These include: hydrogenation catalysts such as $[Rh(diene)(PPh_3)_2]^+$, and $[Rh(diphos)]^+$, olefin dimerization catalysts such as $[Ni(L)_4H]^+$, methylacrylate dimerization catalysts such as $[CpRh(L)(alkyl)]^+$, late transition metal olefin polymerization catalysts such as $[CpCo(L)(alkyl)]^+$, as well as early transition metal olefin polymerization catalysts such as $[ACpZr(alkyl)]^+$, and $[Me_2Si(Cp)(NR)Zr(alkyl)]^+$.

This invention provides new activator compositions comprising polyanionic non-coordinating anionic moieties which can be used to improve the catalytic properties of catalyst cations such as those listed above.

As used herein, the recitation "compatible noncoordinating anion" means an anion which either does not coordinate to a catalyst cation or which is only weakly coordinated to the cation thereby remaining sufficiently labile to be displaced by a neutral Lewis base. The recitation "compatible noncoordinating anion" specifically refers to an anion which when functioning as a stabilizing anion in the catalyst system of this invention does not transfer an anionic substituent or fragment thereof to the cation. Compatible anions are anions which are not degraded to neutrality when the initially formed catalyst complex decomposes. The recitation "metalloid", as used herein describes those elements of the periodic table having metal and non-metal characteristics, including non-metals such as boron, phosphorus and the like which exhibit semi-metallic characteristics. The non-coordinating anionic groups are non-coordinating by virtue of their bulk. They are considered "bulky" when they are too large in size to fit within the coordination sphere of the transition metal cation and thus cannot form strong covalent bonds to the metal center. The recitation "non-ionic core" means a central, support-like material for anchoring or bonding the activator-anions. The anchored anions are then further reacted with a cationic species to form the catalyst system useful for polymerizing monomers. The relation "diradical bridging group" refers to a group of atoms which serve as separator unit(s) or tetering groups between the non-ionic core (T) and the anion activator.

Improvements in activity, selectivity, stability, operability and process adaptability of a catalyst can be realized by use of the non-coordinating polyanionic materials herein described. The improvements can be realized because the polyionic activator composition may be prepared in a variety of molecular shapes and sizes, such as small molecular dianions, or as linear, branched, star or crosslinked polyanionic polymers, or as three dimensional polyanionic particles or objects, each of which shape, charge and molecular size is designed to exert a unique influence on the resulting properties of the final polyionic transition metal catalyst. The polyanionic non-coordinating anions, $[(NCA^{b-})_yT]^{by-}$, comprise a central core composition (T) to which a plurality (y) of non-coordinating anionic pendant groups (NCA) of charge b- are fixed through bonding, such as through covalent bonding. As the size of the core ('T') and the charge (the product of 'b' times 'y') increase the size of the polyanionic core material will become large enough to provide a macroscopic heterogeneous catalyst support. In olefin polymerization systems the heterogeneous catalyst comprising the macroscopic polyanionic non-coordinating anion is capable of controlling product particle size in slurry processes and is amenable to conventional single and series gas phase processes without encountering problems associated with catalyst desorption. Further, the core (T) may serve to immobilize the cationic transition metal catalyst species with respect to flow of reactant into and product out of a reaction zone wherein a catalyzed reaction, such as polymerization, takes place. In this respect, core (T) may be the reactor walls or other immobile surface or surfaces located within the reaction zone.

Polyionic Catalysts In General

Novel classes of poly-non-coordinating anionic compositions as described hereafter can be used to modify and improve the chemical properties (i.e., activity, selectivity, etc.) and physical state (i.e., homogeneous, heterogeneous) of any catalytic system wherein the catalytically active species is a transition metal coordination cation—i.e., a transition metal coordinated to fewer anionic ligands than would fully satisfy the coordination number and charge of the transition metal constituent, thus leaving the transition metal in a positive charge and unsaturated state. The role of a non-coordinating anion in such systems is to balance charge without obstructing the coordinatively-unsaturated site on the active transition metal cation. The conversion of an ionic catalyst system of the form $[Catalyst^{c+}]_{y'}[NCA^{-b}]$ (where $NCA^{b-}$ is a "non-coordinating anion" of the total charge b— such as $BF_4^-$, or $B(Ph')_4^-$; c+ is an integer representing the positive charge on the catalyst and y' is the number catalyst cations required to balance charge) into a polyionic catalyst of the form $[Catalyst^{c+}]_{y'}[(NCA^{b-})_yT]^{by-}$ (where the product of c+ times y'=b times y) can be accomplished by at least two general approaches. First, if the monoionic catalyst $[Catalyst^{c+}]_{y'}[NCA^{b-}]$ is prepared from a catalyst precursor and an ion-exchange reagent, $[Ct^{c+}]_{y'}[NCA^{b-}]$ where the product of c+ times y'=b, then the polyionic catalyst may be prepared by an analogous procedure where the catalyst precursor is reacted with $[Ct^{c+}]_{y'}[(NCA^{b-})_yT]^{by-}$. Alternatively, the preformed mono ionic catalyst can be combined with $[Ct^{c+}]_y[(NCA^{b-})_yT]^{by-}$ under conditions where the desired by-product $[Ct^{c+}]_y[NCA^{b-}]$ and polyionic catalyst $[Catalyst^{c+}]_y[(NCA^{b-})_yT]^{by-}$ can be separated by solubility differences. Thus, if the polyanionic activator is insoluble in a solvent where the monoionic catalyst $[Catalyst^{c+}][NCA^{b-}]$ is stable and soluble, the ion-exchange process can be done by running a solution of the monoionic catalyst down a column of heterogeneous polyionic activator in much the same fashion as is done in conventional ion-exchange chromatography.

Polyionic Olefin Polymerization Catalyst

The olefin polymerization catalysts of this invention are prepared by combining at least one first component which is a derivative of a transition metal of the Group 3-10 of the Periodic Table of the Elements containing at least one ligand (leaving group) which will react with a cation of the second component. The second component contains, pendant from a core component, a plurality of ion-exchange groups each associated with a cation capable of irreversibly combining with the leaving group ligand liberated by the transition first component. Each ion-exchange group comprises a single anionic coordination complex comprising a charge-bearing metal or metalloid element, which anion is chemically bound to the core component and is both bulky and labile, compatible with and essentially non-coordinating toward the transition metal cation formed from the first component, and is capable of stabilizing the transition metal cation without obstructing the transition metal cation's coordinatively-unsaturated and site. Additionally, the anion must be sufficiently labile to permit displacement by an olefin, diolefin or an acetylenically unsaturated monomer during polymerization.

All reference to the Periodic Table of the Elements herein shall refer to that format of the Periodic Table of the Elements, published in *Chemical and Engineering News*, 63(5), 27, 1985 which numbers the groups 1 to 18. Also, any reference to a Group or Groups shall be to the Group or Groups as reflected in this Periodic Table of the Elements. Further, in the formulae which follow, unless otherwise indicated, such lettering which appears which is a symbol for an element is intended to indicate that element, i.e., B means boron, Al means aluminum, Ti means titanium. Letters or groupings of letters not otherwise recognizable as symbols for elements are defined in the formulae, i.e., Ct means a "cation," NCA means a "non-coordinating anion," etc. as defined.

The Transition Metal Component

In general any ligand stabilized transition metal catalyst precursor can be activated to its ionic catalytic state by reaction with a polyionic activator composition of this invention. The same general catalytic attributes observed in a monoionic version of the catalyst will likewise be reflected in the polyionic form of catalyst produced by activation of the catalyst precursor with the polyionic activator compositions of this invention. In a monoionic catalyst system various catalyst performance properties can be influenced by alteration of the ligand structure of the transition metal catalyst precursor, those same ligand affects will likewise be observed in the polyionic catalyst compositions of this invention. However, unlike the monoionic catalyst, in accordance with this invention it is possible to further influence catalyst properties by choice of structure for the anionic moiety of the resulting catalyst. For example wherein the ligand system of the transition metal catalyst precursor is a chiral ligand system which leads to stereochemical control, this same control will be seen in the polyionic catalyst composition of this invention. Yet by reason of selection of the structure of the polyanionic activator the resulting polyionic catalyst may be improved with respect to its activity, molecular weight capability, selectivity, process adaptability and/or by immobilizing the catalyst for fixed bed operation or other catalyst recover processes.

For the olefin polymerization catalyst, the transition metal catalyst precursor is represented by the formula $$(LS)ZX_1X_2$$

wherein Z is a group 3 to Group 10 transition metal; $X_1$ is a leaving group which may be an anionic ligand or a non-coordinating anion; $X_2$ is hydride or a hydrocarbyl radical; and (LS) is a ligand system comprised of one or more ancillary ligands sufficient to complete the coordination number of Z. Since $X_1$ is the anionic leaving group, the final catalyst cation will have the structure $[(LS)ZX_2]^{n+}$ after reaction with the polyanionic activator where n is the charge on the catalyst cations.

For an olefin polymerization catalyst the transition metal catalyst precursor compounds may be any transition metal compound which heretofore has been activatable to a catalytic state for olefin polymerization by an alumoxane. Such transition metal catalyst precursor compounds thus include (but are not limited to) the Group 4, 5 and 6 metal hydrocarbyloxides as described in WO 92/01006; the Group 4, 5 and 6 metal metallocenes as described in European Patent Application 0129368, and U.S. Pat. No. 5,120,867, the Group 4 metal monocyclopentadienyl-heteroatom ligand compounds as described in U.S. Pat. No. 5,055,438, U.S. Pat. No. 5,096,867, U.S. Pat. No. 5,057,475, U.S. Pat. No. 5,026,798 and EPA 416815; the Group 4 metal amido compounds as described in WO 92/12162; the Group 4 metal metallocenes as described in EPA 277,004, and the like. All references mentioned are herein incorporated by reference in their entirety. Those transition metal compounds which are activatable to single sited catalyst systems are the most preferred. These include but are not limited to systems comprising (i) two cyclopentadienyl ligands, each optionally substituted and the two optionally being bridged with a bridging atom or group or (ii) a single, optionally substituted, cyclopentadienyl ligand and a heteroatom—containing ligand, the two ligands optionally being bridged with a bridging atom or group. For example:

1. Monocyclopentadienyl-heteroatom ligand transition metal compounds represented by the formulae:

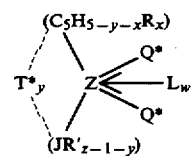

wherein Z is Zr, Hf or Ti in its highest formal oxidation state (+4, $d^0$ complex);

$(C_5H_{4-x}R_x)$ is a cyclopentadienyl ring which is substituted with from zero to four substituent groups R, "x" is 0, 1, 2, 3, or 4 denoting the degree of substitution, and each substituent group R is, independently, a radical selected from a group consisting of $C_1$–$C_{20}$ hydrocarbyl radicals, substituted $C_1$–$C_{20}$ hydrocarbyl radicals wherein one or more hydrogen atoms is replaced by a halogen radical, an amido radical, a phosphido radical, and alkoxy radical or any other radical containing a Lewis acidic or basic functionality, $C_1$–$C_{20}$ hydrocarbyl-substituted metalloid radicals wherein the metalloid is selected from the Group 14 of the Periodic Table of Elements; and halogen radicals, amido radicals, phosphido radicals, alkoxy radicals, alkylborido radicals or any other radical containing Lewis acidic or basic functionality; or ($C_5H_{4-x}R_x$) is a cyclopentadienyl ring in which two adjacent R-groups are joined forming $C_4$–$C_{20}$ ring to give a saturated or unsaturated polycyclic cyclopentadienyl ligand such as indenyl, tetrahydroindenyl, fluorenyl or octahydrofluorenyl;

($JR'_{z-2}$) is a heteroatom ligand in which J is an element with a coordination number of three from Group 15 or an element with a coordination number of two from Group 16 of the Periodic Table of Elements, preferably nitrogen, phosphorus, oxygen or sulfur with nitrogen being preferred, and each R′ is, independently a radical selected from a group consisting of $C_1$–$C_{20}$ hydrocarbyl radicals, substituted $C_1$–$C_{20}$ hydrocarbyl radicals wherein one or more hydrogen atoms is replaced by a halogen radical, an amido radical, a phosphido radical, an alkoxy radical or any other radical containing a Lewis acidic or basic functionality, and "z" is the coordination number of the element J;

each $Q^*$ is, independently, any hydrolyzable anionic ligand such as a hydride, or substituted or unsubstituted $C_1$–$C_{20}$ hydrocarbyl provided that where any $Q^*$ is a hydrocarbyl such $Q^*$ is different from ($C_5H_{4-x}R_x$), or both $Q^*$ together may be an alkylidene or a cyclometallated hydrocarbyl or any other divalent anionic chelating ligand;

$T^*$ is a covalent bridging group containing a Group 14 or 15 element such as, but not limited to, a dialkyl, alkylaryl or diaryl silicon or germanium radical, alkyl or aryl phosphine or amine radical, or a hydrocarbyl radical such as methylene, ethylene and the like;

and L is a neutral Lewis base such as diethylether, tetrahydrofuran, dimethylaniline, aniline, trimethylphosphine, n-butylamine, and the like; and "w" is a number from 0 to 3; L can also be a second transition metal compound of the same type such that the two metal centers Z and Z′ are bridged by $Q^*$ and $Q^{*\prime}$, wherein Z′ has the same meaning as Z and $Q^{*\prime}$ has the same meaning as $Q^*$. Such compounds are represented by the formula:

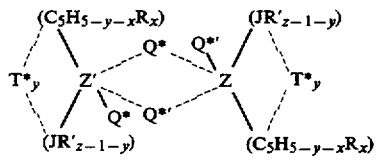

With respect to these compounds the reader is directed to U.S. Pat. No. 5,055,438, U.S. Pat. No. 5,096,867, U.S. Pat. No. 5,057,475, U.S. Pat. No. 5,026,798, and U.S. Ser. No. 07/720,282 and resort thereto may be had for further information about specific compounds within this class which would be most preferred for use.

2. Bis(cyclopentadienyl) Group 4 metal compounds represented by the formulae:

(1.) (A-Cp) $ZX_1X_2$ (2.) (A-Cp) $ZX'_1{}^{x}{}_2$ (3.) (A-Cp)$ZJ'$ (4.) (Cp*) (CpR) $ZX_1$ wherein "Cp" represents a cyclopentadienyl radical which may be substituted or unsubstituted, and:

(A-Cp) is either (Cp)(Cp*) or Cp-A′-Cp* and Cp and Cp* are the same or different cyclopentadienyl ring substituted with from zero to five substituent groups R, and each substituent group R is, independently, a radical which can be hydrocarbyl, substituted hydrocarbyl, halocarbyl, substituted-halocarbyl, hydrocarbyl-substituted organometalloid, or halogen (the size of the radicals need not be limited to maintain catalytic activity, however, generally the radical will be a $C_1$ to $C_{20}$ radical), or Cp and Cp* are a cyclopentadienyl ring in which two adjacent R groups are joined forming a $C_4$ to $C_{20}$ ring to give a saturated or unsaturated polycyclic cyclopentadienyl ligand such as indenyl, tetrahydroindenyl, fluorenyl, or octahydrofluorenyl and A′ is a covalent bridging group which restricts rotation of the two Cp-groups; Z is titanium, zirconium or hafnium; J′ is an olefin, diolefin or aryne ligand; $X_1$ and $X_2$ are, independently, selected from the group consisting of hydride radicals, hydrocarbyl radicals having from 1 to about 20 carbon atoms, substituted-hydrocarbyl radicals having from 1 to about 20 carbon atoms, wherein one or more of the hydrogen atoms are replaced with a halogen atom, organometalloid radicals comprising a Group 14 element wherein each of the hydrocarbyl substitutions contained in the organic portion of said organometalloid, independently, contain from 1 to about 20 carbon atoms and the like; $X'_1$ and $X'_2$ are joined and bound to the metal atom to form a metallacycle, in which the metal atom, $X'_1$, and $X'_2$ form a hydrocarbocyclic ring containing from about 3 to about 20 carbon atoms; and R is a substituent, preferably a hydrocarbyl substituent, on one of the cyclopentadienyl radicals which is also bound to the metal atom.

Generally, any metallocene which has heretofore been activated to a catalytic state by reaction with an alumoxane is also suitable for activation by reaction with a polyanionic activator composition of this invention. Illustrative, but not limiting examples of bis(cyclopentadienyl) Group 4 metal compounds which may be used in the preparation of the improved catalyst of this invention are described in EPA 277,003; EPA 277,004, EPA 416,815, EPA 520,732 and PCT WO 92/00333.

Polyionic Activator Compositions

1. Structural Description of Polyionic Activator (or Catalyst Precursor) Compositions As already noted, the transition metal compound is activated to a catalytically active state by reacting it with a polyionic activator composition which comprises an atomic, molecular, polymeric, or macroscopic core (T) to which are bonded a plurality of non-coordinating anionic pendant groups (NCA $^{b-}$). The structure of the polyionic activator or catalyst precursor compositions comprised of a single type of non-coordinating anions and counter cations can be represented by the following general formula where $Ct^{c+}$ is the counter cation of the total charge c+, y represents the number of pendant NCA-groups; b is the charge on the non-coordinating anion, y' is the number of Ct cations and y times c+ equals y times b:

Polyionic activator compositions can be comprised of a mixture of non-coordinating anions and/or cations with the only requirement being that the final composition has enough cations to balance the charge. The structural requirements for the pendant non-coordinating anions can vary depending on the reactivity of the catalyst cation used in final catalytically active compositions. Thus, it will be appreciated that catalysts based on late transition metal cations may be compatible with a wider variety of pendant NCA's than those based on early transition metal cations.

The anionic portion of a pendant group is chemically bound to the core. By chemically bound, what is meant is a strong bond having greater than 2–3 Kcal and includes covalent, ionic or dative bonds; essentially any bonds other than hydrogen bonds or Vander Waals forces. Preferably the anionic portion of a pendant group comprises a group represented by the formula:

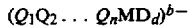

wherein

M is a metal or metalloid selected from the Groups subtended by Groups 3–15; $Q_1$–$Q_n$ are, independently, hydride radicals, halide radicals, disubstituted amido radicals, alkoxide radicals, aryloxide radicals, hydrocarbyl radicals, substituted hydrocarbyl radicals, halocarbyls radicals, substituted halocarbyl radicals, hydrocarbyl and halocarbyl-substituted organometalloid radicals; "n" is the number of Q-ligands bonded to M, "d" is 0 or 1; and preferably no more than one Q being halide, "d" is 1; D is a bridging group such as hydrocarbyl, halocarbyl, substituted hydrocarbyl, hydrocarbyloxy, aryloxy group, oxo or amido which tethers the non-coordination anion to the core T; and b is the charge on the anion. Hydrocarbyl radicals may be those with aliphatic, aromatic or neutral character. Compositions wherein each of the Q-ligands of the anionic pendant group are the same or different aromatic or substituted aromatic radical containing from 6 to 20 carbon atoms are preferred. Each Q is preferably bonded to the metal and may be either a cationic, anionic or neutral ligand. The bridging group can be represented by either Q or D in the activator composition. Generally, a mixed anion and/or mixed cation system may be employed in order to fine tune the desired polymer properties. The metal or metalloids may therefore be the same or different.

An anionic group as above described is analogous in many important respects to the single "non-coordinating anion" (NCA) complex described in EPA 277,004 by which the new ionic-transition metal catalyst system as therein described is produced. In EPA 277,004 the catalyst as taught is a discrete complex comprised of one transition metal cation complexed with one non-coordinating anion. As noted, such an anion is essentially non-coordinating to a transition metal cation; that is, although in non-polar low dielectric solvents the anion is weakly coordinated to the catalyst cation to form a "contract ion pair", addition of a Lewis base (L) such as tetrahydrofuran (THF), amines or olefins readily displaces the anion to form charge separated ionic complexes.

In the single anion catalyst systems as described in EPA 277,003 and EPA 277,004 it was found that the performance of the catalyst correlated to the basicity of the non-coordinating anion. Anionic carboranes as described in EPA 277,003 provide a class of catalyst systems of lower activity and generally produce polymers of lower molecular weight and comonomer incorporation than that class of catalyst systems described in EPA 277,004 which utilize an anionic coordination complex. Anionic carboranes as a class are stronger bases than are anionic coordination complexes as a class.

It was further found that within that class of catalyst systems which are formed with an anionic coordination complex that anion structure exerted a strong influence on the properties of the catalyst. With respect to the most preferred anionic coordination complex, namely the tetra(pentafluorophenyl)boron anion, hereafter referred to as [(pfp)$_4$B]$^-$, replacement of one pentafluorophenyl ligand (pfp) with a hydrocarbyl ligand such as methyl, butyl, phenyl or a polystyrene group produced a catalyst with lower molecular weight and comonomer incorporation capabilities.

Relative to the most preferred class of monoionically activated transition metal catalyst systems, i.e. those wherein [Q$_1$Q$_2$ . . . Q$_n$M]$^-$ is the non-coordinating anion, to further improve the product and process versatility and operability of an ionic catalyst system it has been found to be necessary to have available a wide variety of possible anion structures where the charge, shape, size, and negative charge distribution of the non-coordinating anionic activator composition can be varied.

In this invention, the chemical properties of the activating anion composition are varied by producing it in the form of a polyionic activator composition the molecular core of which can be controlled in terms of its size and shape, as well as providing for control of the extent and position of the negative charge localization within the composition. The polyionic activator compositions can be produced in a range of sizes from that of a simple molecular size for production of soluble catalyst systems to that of macroscopic polyionic activator compositions which are large enough to function as a heterogeneous support for use of the catalyst in fluidized bed, slurry or fixed bed polymerization processes. The polyionic activator compositions comprising a single type of counter cation and pendant non-coordinating anion which are suitable activators are of the formula:

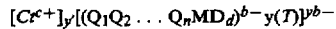

wherein:

Ct is a cation capable of reacting with an early transition metal alkyl complex, such as trialkylammonium, Ag$^+$, Ph$_3$C$^+$, oxonium, or tropylium; M is, a metal or metalloid from Group 3–15; $Q_1$–$Q_n$ are, independently, hydride radicals, disubstituted amido radicals, alkoxide radicals, aryloxide radicals, hydrocarbyl radicals, substituted hydrocarbyl radicals, halocarbyls radicals, substituted halocarbyl radicals, hydrocarbyl and halocarbyl-substituted organometalloid radicals; "n" is the number of Q ligands bonded to M; "d" is 0 or 1 and when "d" is 1, D is a diradical hydrocarbyl, halocarbyl, substituted hydrocarbyl, hydrocarbyloxy or aryloxy, oxo, imido, or sulfido group which teathers the anion to the core T; T is an atomic, molecular, polymeric or macroscopic polyradical moiety capable of coordination with M or with D; "y" is an integer greater than one and represents the number of pendant non-coordinating anions, b is the charge on the anionic pendant groups, c+ is the charge on the counter cation and y' times c+ equals y times b. Polyionic activator compositions may optionally be comprised of a mixture of cations $Ct^{c+}$ and/or pendant anionic groups $(Q_nQ_2 \ldots Q_nMD_d)^{b-}$ with the only requirement being that the number of cations are chosen to balance a charge.

Wherein

T is a polymeric polyradical it may assume any desired shape or size such as a particle, a sheet, a bead, or an object. Polyanion compositions wherein the pendant anionic group is comprised of a Group 4, 5 or 13 element are preferred. Most preferred as the M constituent of the anionic group are boron and aluminum. Particularly preferred for preparation of the catalyst of this invention are polyanion compositions of the formula:

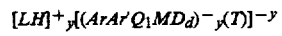
$$[LH]^+{}_y[(ArAr'Q_1MD_d)^-{}_y(T)]^{-y}$$

wherein

T is as previously defined; L is a tertiary amine or phosphine, $LH^+$ is a ammonium or phosphonium salt; M is either aluminum or boron, Ar and Ar' are the same or different aromatic or substituted aromatic radical containing from 6 to about 20 carbon atoms; $Q_1$ is a halide radical, hydride radical, hydrocarbyl, halocarbyl or substituted hydrocarbyl radical containing from about 1 to 20 carbon atoms, an aromatic or substituted aromatic radical containing from 6 to 20 carbon atoms; and D is a hydrocarbyl, substituted hydrocarbyl, halocarbyl, hydrocarbyloxy or aryloxy group, oxo, imido, or sulfido group.

The polyanion composition most preferred for use in preparing catalysts of this invention are of the formula:

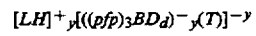
$$[LH]^+{}_y[((pfp)_3BD_d)^-{}_y(T)]^{-y}$$

wherein

B is boron and D is a group of the formula:

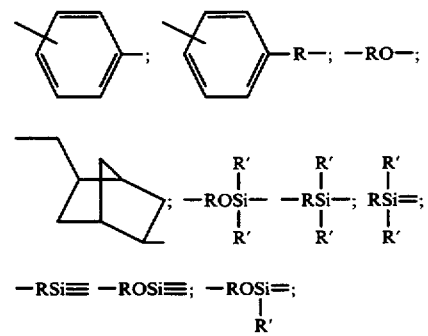

wherein

R is a hydrocarbyl radical.

In general the polyionic activator can be prepared by at least two general synthetic approaches. In one general method, the polyionic activator compound is prepared from a "synthon" compound of the formula $[Ct^{c+}]_y[Q_1Q_2 \ldots Q_nMD']^{b-}$ wherein M, Ct, c+, b−, and $Q_n$ are as previously defined, and D' is a radical group which contains at least one functional group which is polymerizable or otherwise reactive with a substrate (T') to bond therewith, y' is the number of c+ cations and y' times c+ equals b−. The polyionic activator compound is prepared by reacting a synthon compound with a coupling agent polymerization initiator and optionally comonomer, or other substrate (T') under conditions suitable to cause reaction of the D' functional group of the synthon compound to yield $[Ct^{c+}]_y[(Q_1Q_2 \ldots Q_nMD_d)^{b-}{}_yT]^{yb-}$. If necessary, the initial cation, $Ct^{c+}$, can be exchanged for other more reactive cations using standard chemical techniques. In a second general method (where $D_d=D_0$), the polyionic composition can be prepared by reacting the neutral Lewis acid $Q_1Q_2 \ldots Q_nM$ with a polyionic preformed core $[Ct^{c+}]_y[T'']^{y-}$ to form $[Ct^{c+}]_y[(Q_1Q_2 \ldots Q_nM)_yT'']^{y-}$ where T'' is a polyanionic Lewis basic core substrate and y' times c+ equals y−.

A. Synthons

Compounds which are useful for the synthesis of the polyanion compositions as described above are of the general formula:

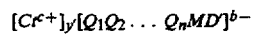
$$[Ct^{c+}]_y[Q_1Q_2 \ldots Q_nMD']^{b-}$$

referred to herein as "synthons" wherein D' is a radical group which contains at least one functional group which is polymerizable or otherwise reactive. A preferred class of the synthon compounds are those of the formula:

$$[LH]^+[ArAr'Q_1BD']^-.$$

The compounds most preferred as synthons are of the formula:

$$[LH]^+[(pfp)_3BD']^-$$

wherein D' is a group of formula:

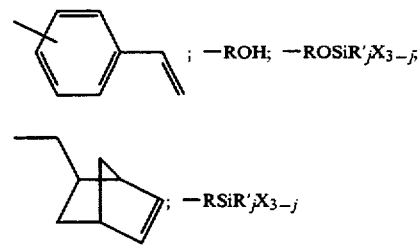

wherein

R is hydrocarbyl such as phenyl, n-propyl, methylenenorbornenyl, or cyclohexyl; each $R_j$ is independently hydrocarbyl or substituted hydrocarbyl, X is a halide or alkoxide and j is an integer between 0 and 2.

B. Preparation of Synthons

Synthons may readily be prepared by reacting a Grignard reagent (BrMgD') with a neutral boron compound (ArAr'Q_1B) to form the solvated MgBr+-salt of the desired functionalized synthon $[ArAr'Q_1BD']^-$. The MgBr+-salt can be easily converted into a variety of desirable Ct+-salts in water, THF, ether, or methylene chloride by treatment with [Ct]+[Cl]− and dioxane (unless water is the diluent, in which case dioxane is not necessary because the desired product is insoluble in water under conditions where the magnesium dihalide dissolves completely). Dioxane is used to facilitate the precipitation of the magnesium halide salt as shown below.

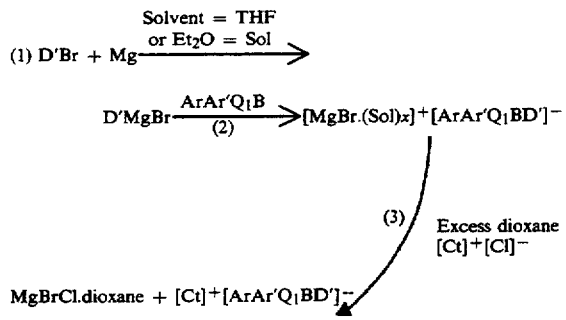

In an alternative method, the Mg and the boron reagents are first combined in an ether solvent (tetrahydrofuran, THF) and the bromide reagent (D'Br) is then added. In this method the Grignard reagent is generated in situ and then is quickly converted by the boron reagent to the stable synthon product.

Production of the synthon compound in high yield through a Grignard reagent intermediate as above described may be accomplished under those conditions of temperature and with those solvents which are conventionally used in preparing a Grignard reagent. As is known to those skilled in the art of Grignard reactions, if the bromide reagent contains other functional groups which are adverse to the formation of a Grignard reagent, such as for example a hydroxide group, it must first be converted to a Grignard non-reactive group such as a trimethylsiloxane or a tetrahydropyranyl ether (THP) group, i.e., if D' has any sensitive groups, they must first be "protected". One of ordinary skill in the art can employ standard organic protecting group concepts in this invention. For example, 4-bromostyrene and bromonorbornylene may be used without further modification in the preparation of the Grignard intermediate reagent whereas 3-bromopropanol cannot. It would be necessary to use a protected bromopropanol to form an stable Grignard reagent.

The initially formed MgBr+-salt can be converted into a more well-behaved Ct+-salt such as a Li+, Et$_4$N+, or trialkylammonium-salt, using standard metathetical procedures including ion-exchange chromatography. Thus, the initially formed MgBr.(THF)$_x$+ salt of the synthon may be converted into the Li+, Na+, or Ct+ − salt by running a solution of magnesium bromide-precursor down a cation-exchange column containing a commercially available ion-exchange resin, such as Amberlyst XN-1010 or Amberlite IRP-69 resin, [a registered trademark of Rohm and Haas Co., located at Independenate Mall West, Philadelphia, Pa., 19105 Phone: (215) 592-3000] which has been pretreated or loaded with the desired cation. The procedures for pretreating and using ion-exchange resins are well-established and may be employed in this invention. These salts are preferred over the MgBr+-salt because they can be isolated as crystalline products and because they can be more easily converted into the final polyanionic form. The preparation of several salts of (pfp)$_3$B(4-styrene)− and (PfP)$_3$B(methylenenorbornylene)− are given in the Examples Section. The preparation of an alcohol functionalized synthon can be accomplished in a similar fashion using a THP-protected alkylhalide. The Grignard reagent is formed in THF, and the anion is prepared from the stable protected Grignard reagent by treatment with B(pfp)$_3$. Conversion of the MgBr+-salt into the trialkylammonium salt can be done in water using excess ammonium halide. In many cases these conditions are sufficient to catalyze the deprotection of the alcohol and the final alcohol functionalized synthon [R'$_3$NH][(pfp)$_3$B-R-OH], can be formed in one step.

Silylhalide functionalized synthons can be prepared from the norborylene- and styrene-functionalized synthons using standard hydrosilation procedures as indicated in FIG. 1 routes 4 and 5. Likewise, the alcohol functionalized synthons can be converted into silylhalide analogs by treatment with R'$_j$SiCl$_{4−j}$ (j=0 to 3) and tertiary amine (to adsorb the liberated HCl) as in FIG. 1 route 6 to synthon 6.

2. Preparation of Polyanion Compositions From the Coupling or Polymerization of Synthons Synthon compounds may be converted to a polyanion composition by well established synthetic techniques such as anionic, cationic, free radical, ring opening (ROMP), conventional Ziegler-Natta and metallocene based olefin polymerization catalysis, as well as by an assortment of hydrolysis and other 'condensation' reactions. FIG. 1 depicts in summary fashion some of the variety of techniques by which a synthon compound may be converted to a polyionic activator composition.

As illustrated by FIG. 1 a synthon may be polymerized or copolymerized to yield a variety of specifically shaped polyanion compositions. It should be appreciated by those of ordinary skill in the art that there are literally an infinite number of chemical methods available for coupling, or polymerizing substituted norbornylenes, styrenes or alcohols to form a discrete or polymeric material. Most of this art was applied to simple, non-ionomeric monomers. This invention couples or polymerizes monomers which are bulky and have a net negative charge. If charge or steric bulk prematurely stop polymer growth, a few equivalents of a neutral spacer comonomer can be added to allow further activator polymerization. It should be noted that in some cases living anionic and living ROMP [ring opening metathesis] polymerization techniques can be employed to create block, star, and end functionalized polyionic activators.

Polyanions meeting the design criteria can be prepared by a variety of chemical approaches. This concept described herein provides a continuum of catalyst systems ranging from homogeneous to heterogeneous as the size and charge of the polyanion increases. At some point in each of the described approaches the polyanionic activator can be prepared as a macroscopic particle which itself can function as a heterogeneous support in slurry, bulk gas phase, processes and fixed bed. When linear polymers are prepared the individual polyanionic units can entangle or aggregate together to form macroscopic particles that function as both activator and catalyst support.

The following are illustrative, but not limiting, examples of techniques for preparing polyanion compositions having specific features of size, shape and charge distribution.

A. Polyionic Activators From Norbornylene Functionalized Synthons

As indicated in FIG. 1 routes E and F, norbornylene terminated synthons can be converted into linear or crosslinked polymeric polyanions using catalysts and initiators which are known to affect the polymerization or copolymerization of common norbornylene derivatives. Substituted norbornylenes can be polymerized by cationic, Ziegler-Natta, ring opening metathesis and Group 4 metallocene olefin polymerization catalysts. In each case, the structure of the polyionic activator composition (linear or crosslinked) and the concentration of pendent ionic centers can be controlled by use of various amounts of comonomers (such as norbornylene) and/or crosslinking agents (such as norbornadiene) during the polymerization reaction. FIG. 1 routes E and F begins with a synthon in which the methylene norbornylene functionality is directly bonded to the boron anion through the methylene [where "SP" is the spacer unit and is illustrated equal to zero], or through a suitable spacing moiety, 'SP'. The spacing unit 'SP' serves to bridge the functional groups of the system to the boron center and is a hydrocarbyl or halocarbyl diradical containing from about 1 to 10,000 carbon atoms such as methylene or polystyrene. As discussed above, the norbornylene functionalized synthon can be isolated with a variety of counter cations. It will be appreciated by those of ordinary skill in the art that the cation in the synthon needs to be chosen so as to avoid potential incompatibilities with the particular polymerization system being used in the preparation of the polyionic activator. Thus, when preparing a polyionic activator using an olefin polymerization catalyst one must avoid the presence of labile Lewis Bases which may be associated with the counter cation (for example $MgBr·(THF)_x$). The choice of counter cation may also play a role in the thermal stablilty of the synthon salt.

The homopolymer of the synthon [DMAH][B(pfp)$_3$nb] (where DMAH=PhMe$_2$NH+, and nb=methylene-norbornylene) was prepared by the addition of a catalytic amount of Cp$_2$HfMe$_2$ (where Cp is cyclopentadienyl and Me is methyl). The hafnocene precursor reacts with a portion of the synthon to produce an active olefin polymerization catalyst [Cp$_2$HfMe(NMe$_2$Ph)][B(PfP)$_3$nb] which slowly catalyzes the polymerization of the anions through the unsaturated norbornylene substituent to produce a glassy low molecular weight linear polyionic activator.

In many cases when the spacing unit 'SP' is small or non-existant the functional groups, such as norbornylene, may be so close to the charge bearing center (i.e. the boron atom) that the chemistry of the functional group is affected. As the size of 'SP' increases the chemistry of the functional groups becomes standard and the desired polyanion can be synthesized using established procedures. The norbornylene synthon, [Et$_4$N]+[B(pfp)$_3$(ST$_{yn}$)−nb)]− where (ST$_{yn}$) represents polystyrene can be prepared in a three step procedure starting from lithium methylene norbornylene as shown below

[Et$_4$N][B(pfp)$_3$(SP−nb)] (where 'SP' is a linear polymer such as polystyrene) can be copolymerized with ethylene in toluene at low pressure by the addition of a small amount of a ionic hafnium catalyst [(Cp$_2$HfMe(N-Me$_2$Ph)][B(pfp)$_4$]). The granular ethylene copolymer can be washed with methylene chloride containing excess [DMAH][Cl] to exchange DMAH+ for Et$_4$N+ and form the final polyionic activator. Similar procedures can be employed to prepare polyionic activators derived from other polyolefin backbones by proper choice of catalyst (chiral metallocene and propylene for isotactic backbones, or fluorenyl-based metallocenes for syndiotactic backbones) and monomers. As indicated in FIG. 1 route 5, the norbornylene synthon may also be converted into polyionic activators using hydrosilation chemistry (i.e., platinum oxide catalysts and HSiR$_j$X$_{3−j}$) to introduce a silicon halide or alkoxide functionality (i.e. X) on the norbornylene substituent followed by various hydrolysis procedures (see FIG. 2 and 3).

B. Polyanions From Styrene Functionalized Synthons

As illustrated in FIG. 1, route D, a styrenic synthon may be polymerized by a variety of techniques to yield a polyanion composition of various properties. Again, 'SP' is defined as a spacing unit containing from about 1 to 10,000 carbon atoms bridging the boron anion to the functional groups. These include the homo- or copolymerizations via free-radical, cationic, anionic or thermal mechanisms. The use of emulsion polymerization technology in combination with the free radical polymerization process can be designed to yield microporous polyanionic polymeric gels or bead compositions. The synthesis of a synthon reagent having styrenic functionality is straightforward from 4- bromostyrene, magnesium, and B(pfp)$_3$. A variety of polyanionic crosslinked polymers are accessible by the free radical, cationic, or anionic polymerization of a styrenic synthon reagent in the presence of divinylbenzene. Again, there are many opportunities for synthetic control over the size, topology, charge and porosity of the final product.

The staged addition of styrenic synthon monomer at the end of the polymerization of the crosslinking reagent will allow for the formation of a "skin" or surface concentrated content of fluorinated activator coating the exterior of the styrenic micropores.

Another important use of this synthon is to convert the pendent styrenic olefin into a silicon halide or alkoxide using a silane, $HSiR'_jX_{3-j}$, where X is alkoxide or halide and a standard hydrosilation catalyst as shown in FIG. 1, route to complex 4. The use of silyl halide or alkoxide coupling reagents to prepare polyanionic activators is discussed in the next section.

C. Polyionic Activators From Hydroxy-Functionalized Synthons

As indicated in FIG. 1, route A, hydroxy functionalized synthons can be used to prepare discrete polyanions by reaction with metallic halides in the presence of an HCl trap such as trialkyl amines. Thus, the trianion, $[PhSi(OPh-(SP) B(PfP)_3)_3]^{3-}$, can be prepared by reacting $PhSiCl_3$ with three equivalents of $[Ct]^+[B(pfp)_3(SP-PhOH)]^-$ in the presence of poly-4-vinylpyridene. Other approaches for preparing polyionic activator compositions from hydroxy functionalized synthons include: acid catalyzed dehydration of hydroxylated surfaces (such as amorphous silica and mineral silicates), and esterification or transesterification of discrete or polymeric materials containing more than one carboxylic acid or ester per molecule, polymer chain or particle.

D. Polyanions From Silylhalide Functionalized Synthons

Figure 2:
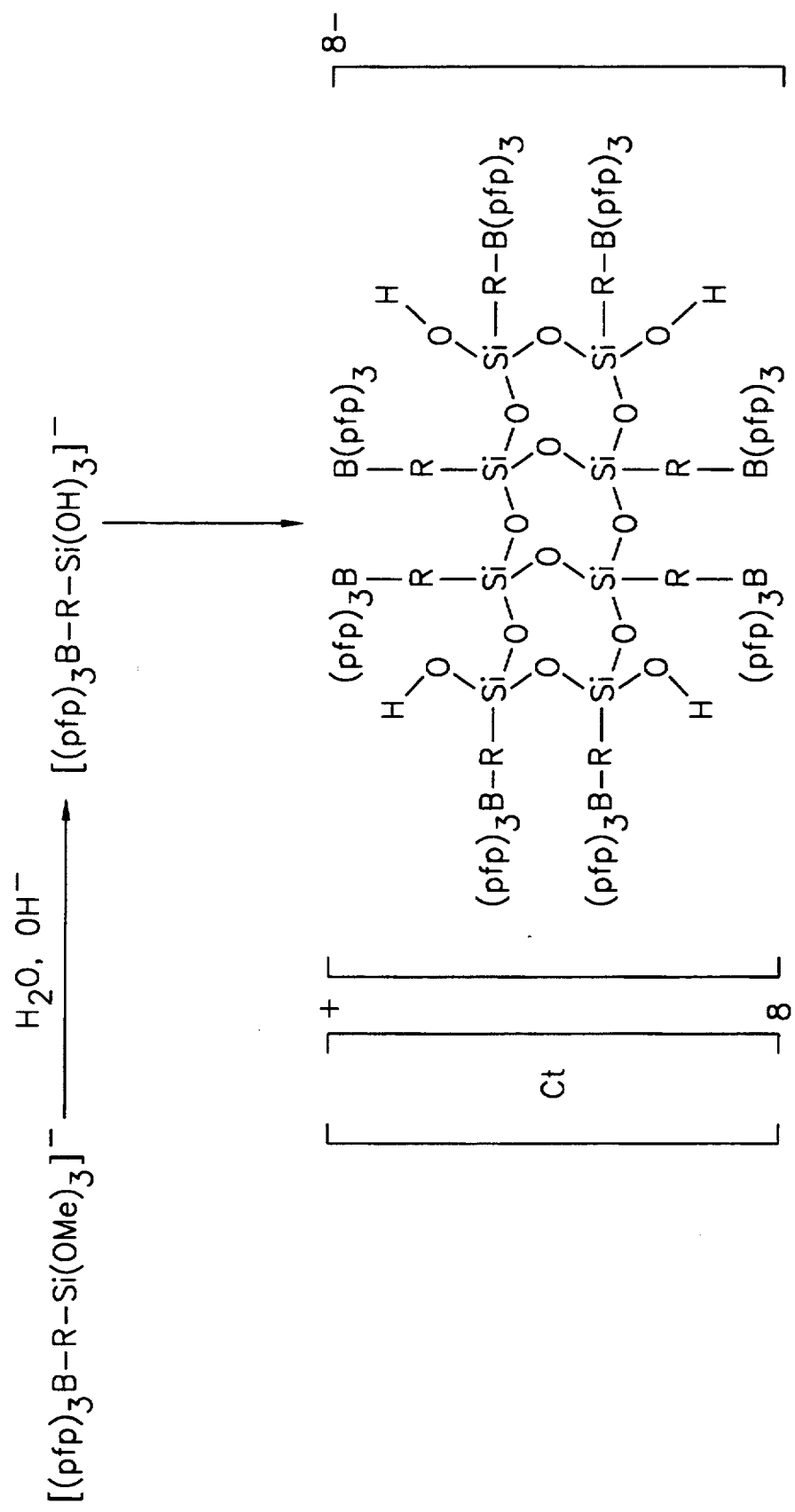
FIG. 2 depicts the structure of a polyanionic silicate activator composition which can be produced in accordance with this invention.
Figure 3:
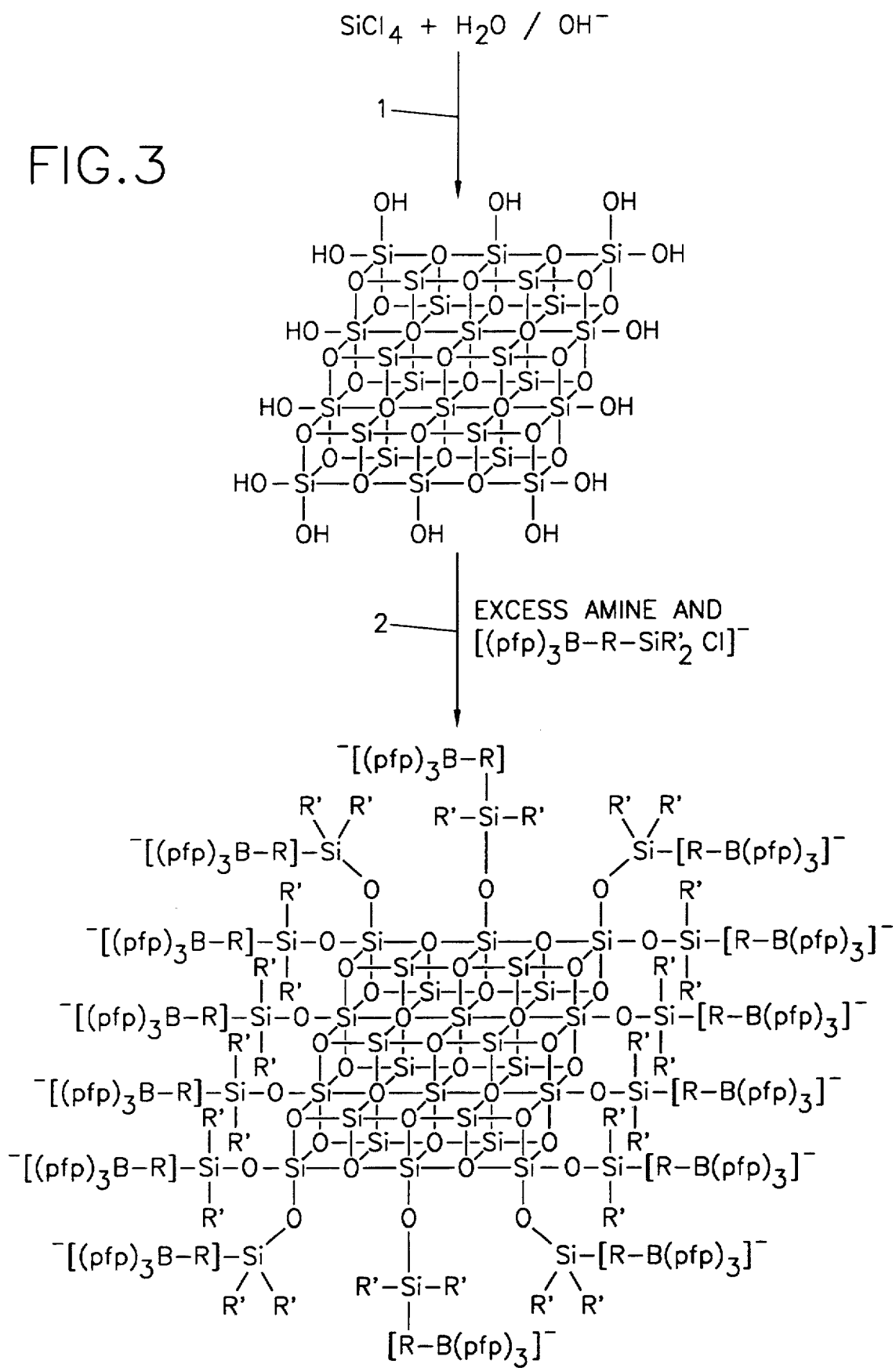
FIG. 3 is a silica particle which can be prepared to have a polyanionic activating skin in accordance with this invention.

As illustrated by FIG. 1, routes C and B and FIGS. 2 and 3 polyanionic compositions can be prepared from synthons with silyl halide or alkoxide functionalities. This part of the invention utilizes well established fields of organometallic and solid state synthesis to prepare novel polyionic activator compositions from the special ionomeric monomers or synthons described above.

The synthesis of silicates by the controlled hydrolysis of $R'_jSiX_{4-j}$ is a well developed field of technology when R' is a normal organic substituent such as methyl or phenyl. The physical properties of the resulting crosslinked polymer can be controlled by adjusting the ratios of the monomer components (i.e. the amount of $SiX_4$, $R'SiX_3$, and $R'_2SiX_2$ etc.). A continuum of polymeric materials can be prepared which range from brittle inorganic solids (monomers where j=0 or 1) to rubbery organometallic polymers (where a significant amount of j=2 and 3 chlorosilane monomers are added). Other important structural variables such as molecular weight and sequence distribution of comonomers can be controlled by adjusting the pH, the concentration, temperature and time of reaction (for $M_w$ control), and staging or sequencing the addition of comonomer (for sequence distribution control). Most of the work on the classical systems of polysilicate synthesis was carried out using water as the solvent and the final products are poorly defined silicate materials known as "sol-gels". More recently polysilicates have been prepared by the controlled hydrolysis of silylhalides in organic solvents such as toluene, or methylene chloride. The results of this more recent procedure indicates that silicate synthesis in organic solvents using stoichiometric amounts of $H_2O$ (needed to convert the silylhalide to the silanol) can be a more selective and reproducible method of preparing low molecular weight materials than analogous reactions carried out in basic water. This technology can be used to form polyanionic compositions by preparing and hydrolyzing anionic coupling reagents $(NCA)_jSiX_{4-j}$ where NCA preferably is $[(pfp)_3B-D-]^-$. The distance from the boron atom to the silicon atom in the coupling reagent can be varied over a large range by replacing "bridging group" (—SP—) with linkages of different size such as phenyl, propyl, biphenyl, and styrene oligomers. A simple example of this concept is for the controlled hydrolysis of $[pfp)_3B-SP-PhSi(OMe)_3]^-$ as shown in FIG. 2. The reaction in FIG. 2 and FIG. 3 are included for the purposes of clarifying the concept and are not intended to indicate that single, well defined polyanions, would be produced under hydrolysis conditions.

The reaction can also be carried out in the presence of neutral, smaller comonomers such as $CF_3CH_2CH_2Si(OMe)_3$ to control or modify degree of polymerization and total charge. The polymerization process may yield polyanion compositions having exposed and reactive Si-OH groups. The exposed silanol groups can be protected with smaller organosilicon head groups such as $CF_3CH_2CH_2SiMe_2X$. Another level of control is to do sequential additions of a neutral silicon halide crosslinking agent and a synthon reagent. A simple and potentially useful example would be to create a central crosslinked core (T) by the controlled hydrolysis of $SiX_4$ followed by the delayed addition of synthon agent to "cap" the outermost silicon hydroxyls on the central core with non-coordinating anions to form small particles of silica (T) with anions on the "skin" as shown in FIG. 3, where R represents the bridging spacer unit and the functional lead group. The silicates depicted in FIG. 3 are intended to represent a slice of three-dimensional solid which may be prepared under hydrolysis conditions. The hydroxy- and activator functional groups on the silicon atoms which are not located in the plane of the paper have been excluded for the purposes of clarity.

As illustrated by FIG. 1, view C, a synthon may be coupled to a wide variety of hydroxylated substrates such as silica gel, alumina, metal oxides, polymers, or membranes which have polyhydroxylated surfaces. FIG. 1B shows how silyl halide or alkoxide anionic coupling reagents 4, 5 or 6 can be polymerized using standard hydrolysis procedures to give linear, branched or crosslinked polyanionic siloxanes or siliates.

Figure 4:
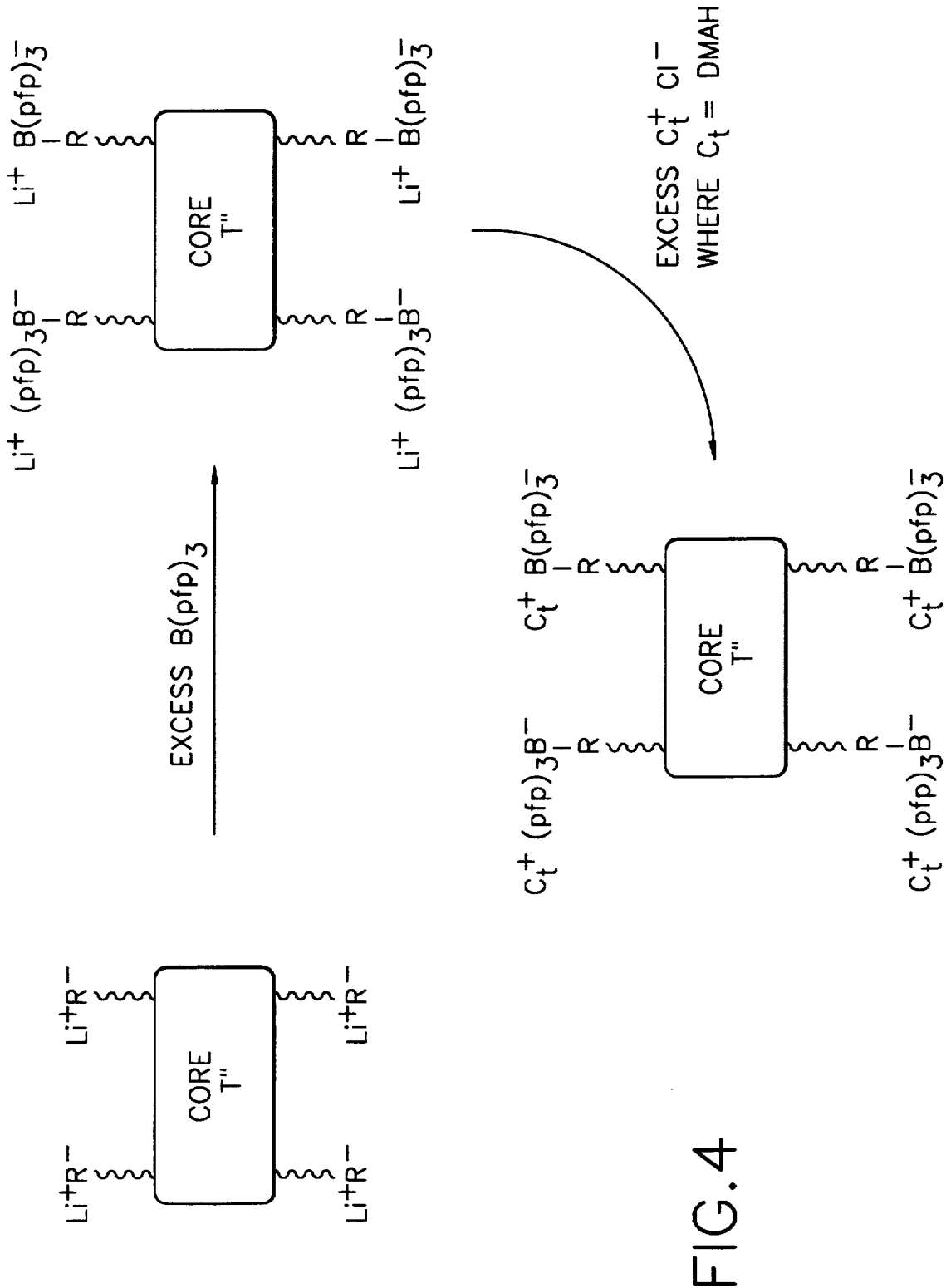
FIG. 4 illustrates one method of preparing polyionic activator compositions by reaction with a preformed polyionic core.

3. Preparation of Polyionic Activators From Preformed Polyionic Core Substrates The second general method of preparing polyionic activators involves the reaction of a preformed polyionic core $[Ct^{c+}]_y[T''^y]$ with an excess of a suitable Lewis Acid, as shown in FIG. 4, where $C+^{c+}$ is lithium cation and the neutral Lewis Acid is $B(pfp)_3$. This approach can be used to prepare a wide variety of descrete and heterogeneous polyionic activator compositions. The synthetic approach will yield useful polyionic activators from any preformed polyionic core precursor if two design criteria are met: 1) the anionic pendent group —R— (as shown in FIG. 4) must be sufficiently basic to from a stable coordination complex with $B(pfp)_3$ and 2) the substrate T'' must not contain accessible chemical functionalities which act as catalyst poisons. The chemical compatibility of a particular core T'' with the metallocene catalyst cation, and the reactivity of a selected pendent group —R— with the Lewis Acid ($B(pfp)_3$) are easily predicted using known reactivity patterns. If it is chemically reasonable that the model compound $[Ct]^+[H-R]^-$ would react with $B(pfp)_3$ to form a stable salt $[Ct]^+[B(pfp)_3(R-H)]^-$, and if the resulting boron anion would be expected to function as a stable non-coordinating anion in the metallocene catalyst system (i.e. if B(pfp)$_3$(R—H)$^-$ is stable to hydrolysis by water) then the scheme shown above will yield a suitable polyionic activator (unless the core T″ is itself a catalyst poison). Core substrates which expose high concentrations of chemical functionalities which are known poisons for metallocene polymerization catalysts (polar functionalities such as carboxylates, acid protons, organic halides, esters, ketones, aldehydes etc.) should be avoided. In some cases, such as when silica is the substrate and hydroxyl-groups are present on the surface, the reactive functionality can be masked or protected using standard chemical treatments.

Illustrative but not limiting examples of polyionic activators prepared from preformed core substrates are described below.

A. From Crosslinked Polystyrene Core Substrates

Figure 5:
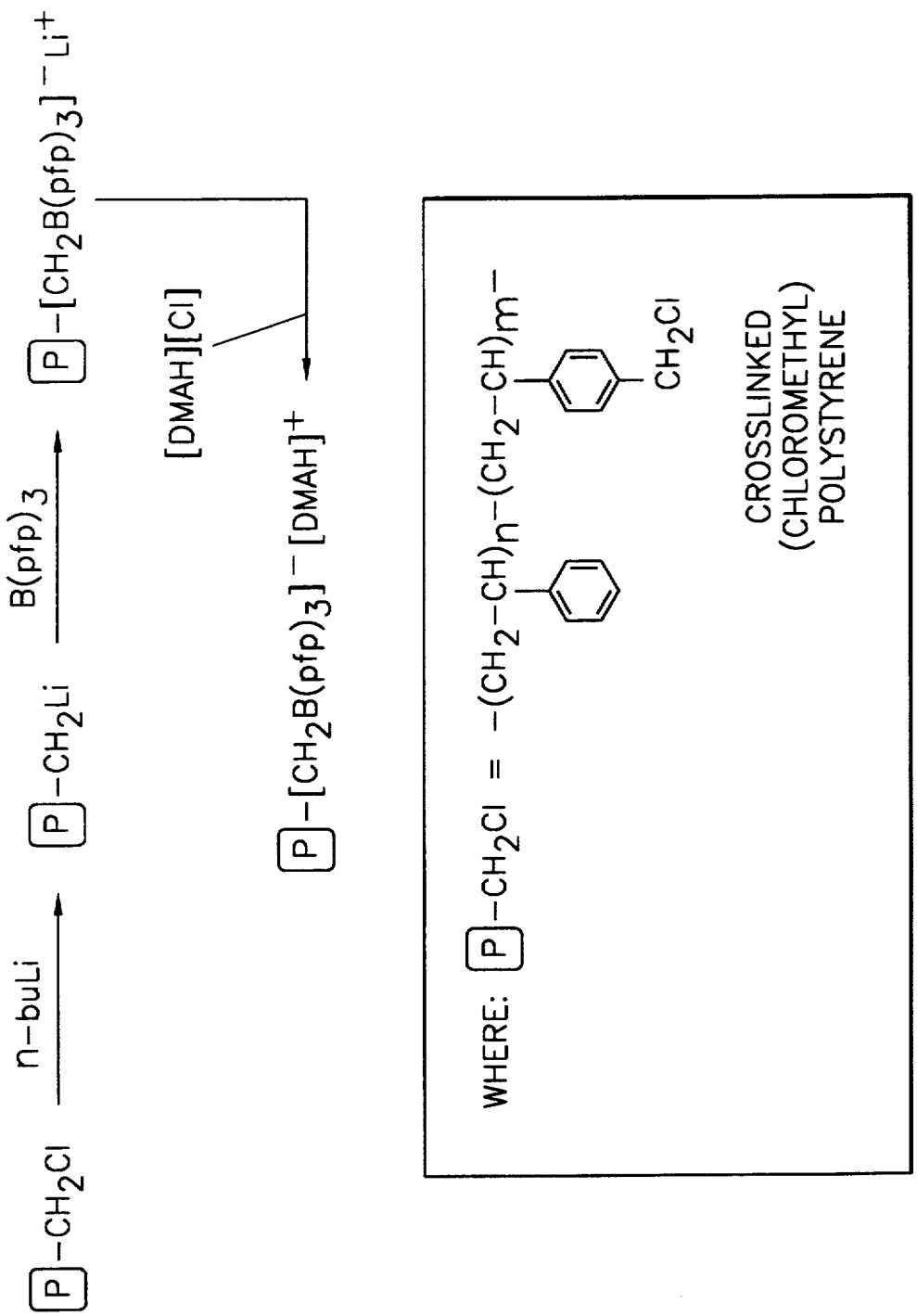
FIG. 5 illustrates a method for producing a variety of microporous polystyrene polyionic activator compositions.

Polystyrene supported polyionic activators can be prepared by two distinct methods. The first approach involves modification of preformed crosslinked polystyrene beads which can be purchased or prepared using emulsion polymerization procedures. The general approach is shown below for a crosslinked styrene/chloromethylstyrene copolymer. Lithiated polystyrene beads can be prepared by a variety of established procedures. When the chloromethylstyrene copolymer is used lithiation yields pendent groups having a benzyl anion structure and it is known that benzyl anions (e.g. BzLi) form stable anionic coordination complexes with B(pfp)$_3$. Thus, a variety of microporous polystyrene polyionic activators can be prepared using the scheme shown in FIG. 5.

Figure 6:
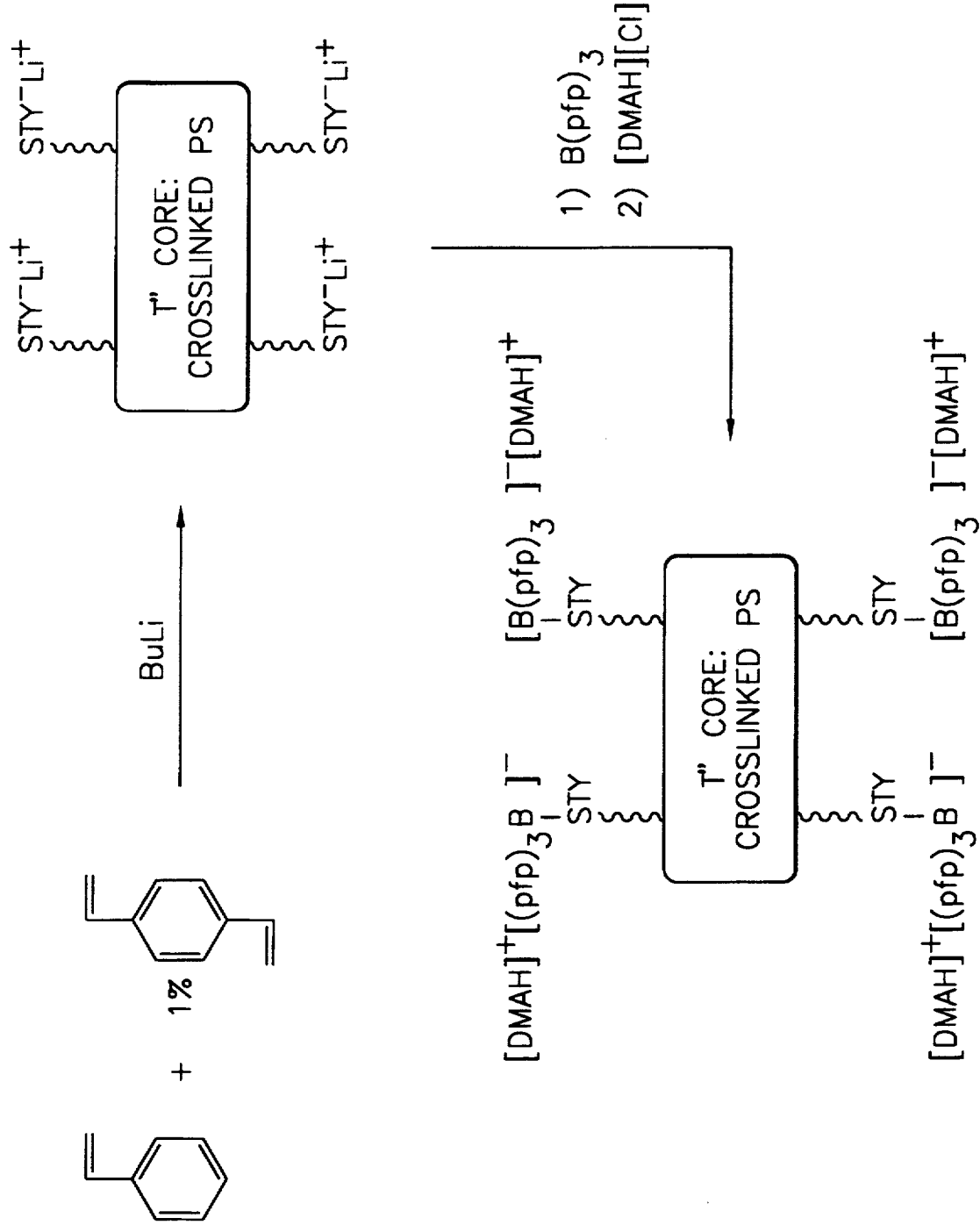
FIG. 6 illustrates an anionic polymerization technique for preparing a cross-linked polystyrene with pendent living lithium polystyrene groups.

A second general approach for preparing polyionic activators containing crosslinked polystyrene substrates is to use anionic polymerization techniques to prepare a crosslinked polystyrene (or other anionically prepared polymer backbone) core with pendent living lithium polystyrene groups as shown in FIG. 6. This approach is quite general and will work for any polymer backbone which can be synthesized using living anionic polymerization techniques. The size, concentration of pendent ionic groups, and the physical properties of the core T″ can be varied by adjusting the amount of crosslinking agent, the monomer to initiator ratio, the solvent, the concentration of monomer, the selection of monomer(s), and the time of reaction in the core forming step.

B. From Polydivinylbenzene Core Substrate

Figure 7:
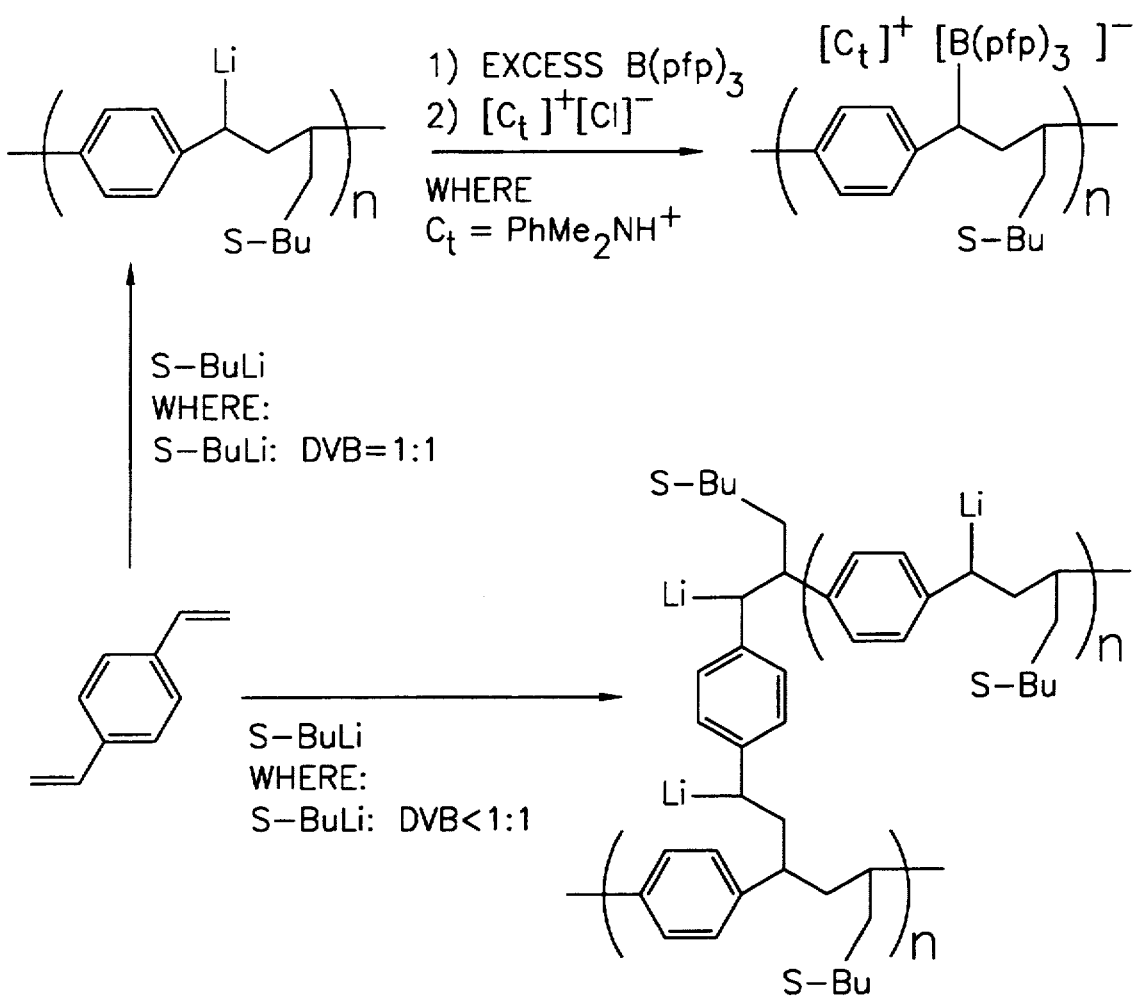
FIG. 7 illustrates how linear and cross-linked lithiated polymers can be prepared using divinylbenzene and an anionic initiator.
Figure 7:
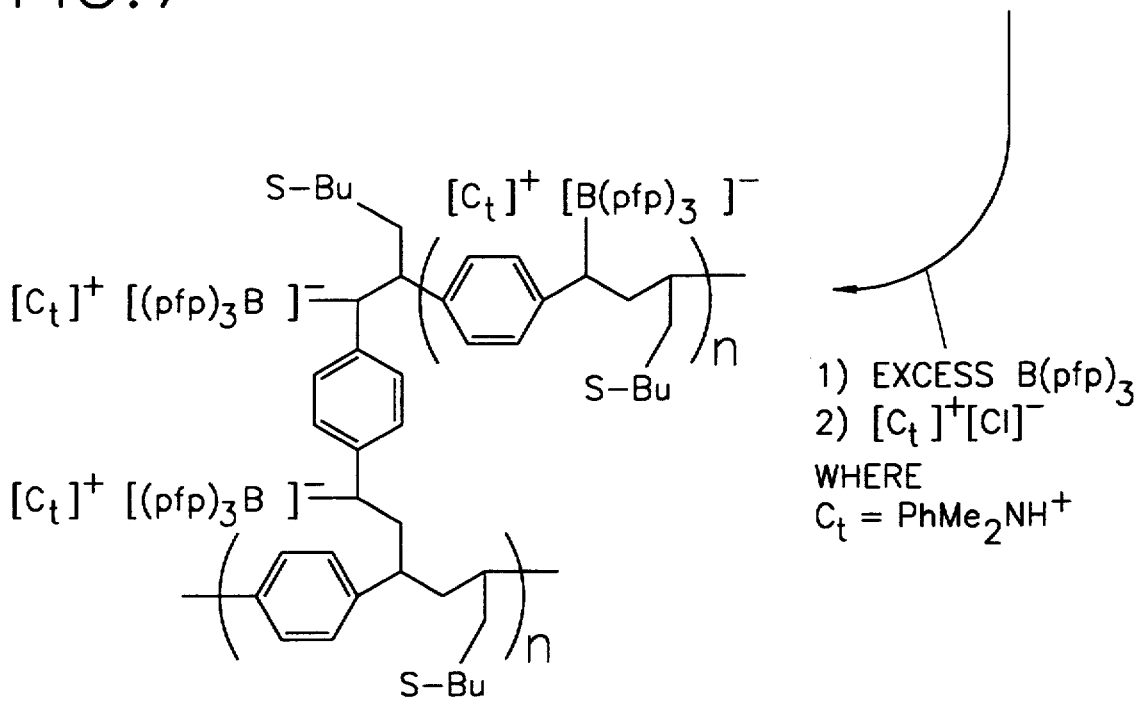

The scheme FIG. 7 shows how linear and crosslinked lithiated polymers can be prepared using divinylbenzene and an anionic initiator. The molecular weight of the final product can be varied by adjusting the reaction time, temperature, and solvent. Long reaction times, higher temperatures and better solvents yield higher molecular weight products. Reaction of the lithiated polymer with excess Lewis Acid (preferability B(pfp)$_3$), followed by the standard [DMAH][Cl]treatment yields polyionic activators, as illustrated in FIG. 7 where DVB represents divinylbenzene.

C. From Surface Modified Glass, Silicas, and Metals

Figure 8:
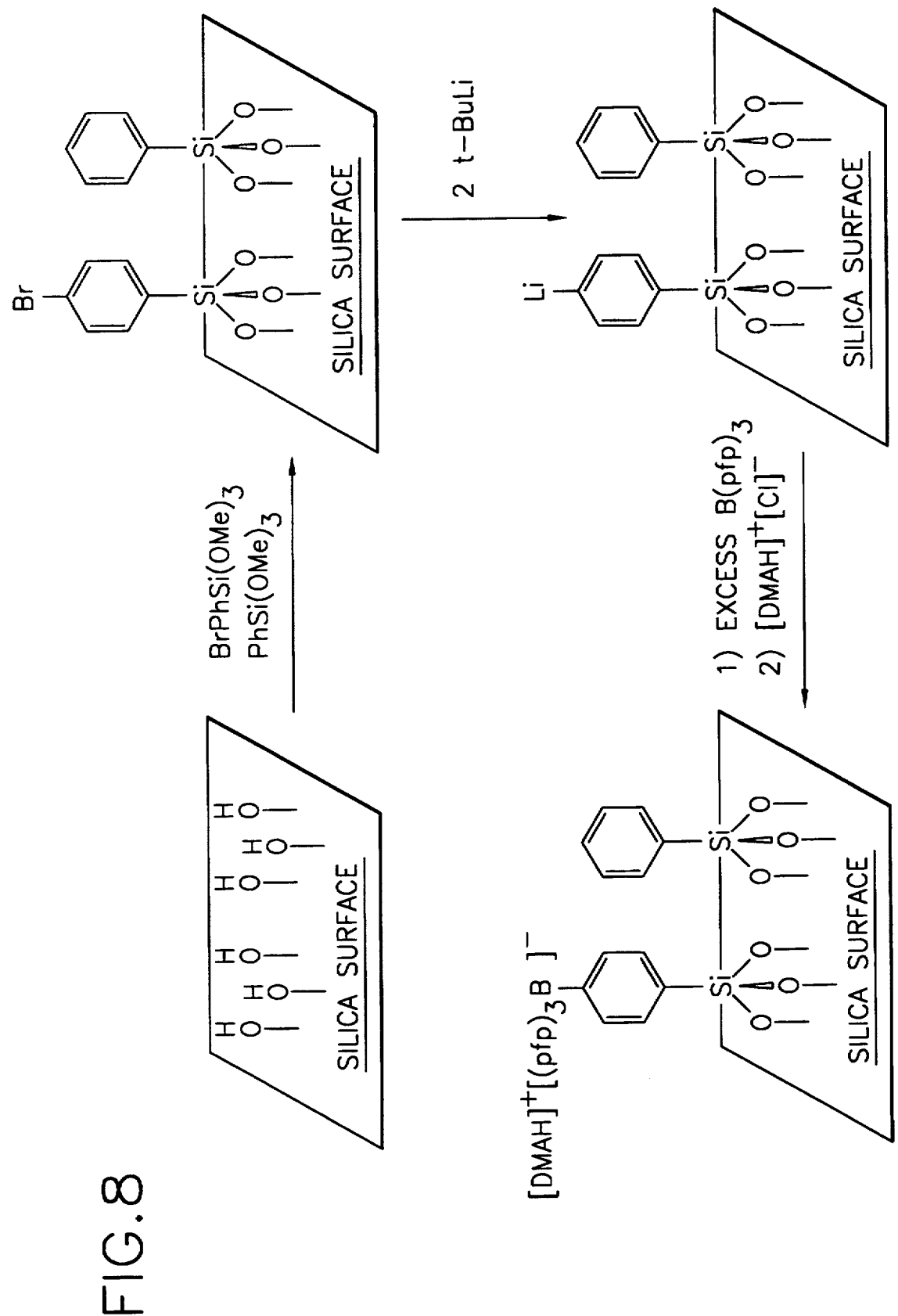
FIG. 8 illustrates a method for preparing a polyanionic composition from a surface modified glass, silica or metal substrate.

The use of silane coupling reagents of the form R$_x$SiX$_{4-x}$ (where each R is an organic radical and X is either halide or alkoxide) to modify the hydroxylated surface of glass or silica is a well established field. This technology can be sued to coat the surface of hydroxylated surfaces with a wide variety of R-functionalities. The scheme illustrated in FIG. 8 exemplifies a bromobenzene functionality covalently bonded to a silica surface using a mixture of BrPhSi(OMe)$_3$ and PhSi(OMe)$_3$. The concentration of bromobenzene functionality can be varied by adjusting the ratio of the two silicon coupling reagents. Treatment of the surface modified silica with excess t-BuLi in ether or THF at −78° C. converts the bromobenzene functionality into a basic aryllithium reagent. The reaction is filtered, washed with THF or ether, suspended in ether, and treated with excess B(pfp)$_3$. The solid is isolated by filtration, washed with excess toluene, dried and placed in a narrow chromatographic column. The silica is slowly eluted with a THF solution of [DMAH][Cl] (large excess) to affect the exchange of DMAH-cation for the lithium counter-ion. The column is then eluted with a large excess of pure methylene chloride to remove excess [DMAH][Cl] and coordinated THF. The product is dried in vacuum at elevated temperature for 24 hours yielding a polyionic activator where the core T has a high surface area of silica. Similar procedures may be used to prepare polyionic activators from other hydroxylated surfaces such as glass, alumina, or polymers containing hydroxide-functionality such as aluminum, zirconium, tin, titanium, and nickel.

4. Preparation of the Catalyst System

The improved catalyst compositions of the present invention will, preferably, be prepared in a suitable solvent or diluent. Suitable solvents or diluents include any of the solvents known in the prior art to be useful as solvents in the polymerization of olefins, diolefins and acetylenically unsaturated monomers. Suitable solvents include but are not necessarily limited to, straight and branched-chain hydrocarbons such as isobutane, butane, pentane, hexane, heptane, octane and the like; cyclic and alicyclic hydrocarbons such as cyclohexane, cycloheptane, methylcyclohexane, methylcycloheptane and the like and aromatic and alkyl-substituted aromatic compounds such as benzene, toluene, xylene and the like. Suitable solvents also include liquid olefins which may act as monomers or comonomers including ethylene, propylene, butadiene, cyclopentene, 1-hexane, 3-methyl-1-pentene, 4-methyl-1-pentene,1,4-hexadiene, 1-octene, 1-decene and the like. Suitable solvents further include basic solvents which are not generally useful as polymerization solvents when conventional Ziegler-Natta type polymerization catalysts are used such as chlorobenzene.

In general, and while most transition metal compounds identified above may be combined with most activator compounds identified above to produce an active olefin polymerization catalyst, it is important to continued polymerization operations that either the metal cation initially formed from the transition metal compound, or a decomposition product thereof, be a relatively stable catalyst. It is also important that the anion of the activator compound be stable to hydrolysis when an ammonium salt is used. Further, it is important that the acidity of the activator compound be sufficient, relative to the transition metal compound, to facilitate the needed reaction of the cation portion of the activator with a ligand of the transition metal compound. Conversely, the basicity of the transition metal compound must also be sufficient to facilitate the needed reaction. In general, transition metal compounds which can be hydrolyzed by aqueous solutions can be considered suitable compounds for forming the catalysts described herein.

As before discussed, the active catalyst species of the catalyst of this invention is relatively stable and is not subject to the ion equilibrium deactivation as are alumoxane cocatalyzed transition metal catalyst systems. Unlike metallocene-alumoxane catalyst systems wherein, to obtain a practical level of catalyst productivity it is generally required to use an amount of alumoxane, measured as aluminum atom, to provide a ratio of Al:transition metal well in excess of 1000:1, catalysts of this invention which are highly productive may be prepared at ratios of metallocene to activator in an amount which provides a ratio of metallocene molecules to a number of pendant anion groups of the activator composition of 10:1 to about 1:1, preferably about 3:1 to 1:1. The degree of "polyanionicness" of an activator composition—i.e., the number of pendant anionic groups contained by a given quantity of activator compositions—may be readily determined by titrating an aqueous solution of it to a neutral pH with a base such as NaOH.

In general the catalyst system of this invention can be prepared by combining a transition metal compound or metallocene having (i) at least one substituent ligand which is hydrolyzable with water or (ii) at least one leaving group ligand, with a polyanion activator composition as described above which generally comprises a core (T) having a plurality of covalently pendent non-coordinating anionic groups the charge of which is balanced by a plurality of cations which are reactive with the leaving group ligand of the transition metal compound in a suitable hydrocarbon solvent at a temperature within the range of from about −100° C. to about 300° C., preferably from about 0° C. to about 100° C., and allowing the two components to react.

In general, the stable catalyst formed by the method of this invention may be separated from the solvent and stored for subsequent use. The less stable catalyst, however, will, generally, be retained in solution until ultimately used in the polymerization of olefins, diolefins and/or acetylenically unsaturated monomers. Alternatively, any of the catalysts prepared by the method of this invention may be retained in solution for subsequent use or used directly after preparation as a polymerization catalyst. It will, of course, be appreciated that the catalyst system will form in situ if the components thereof are added directly to the polymerization process and a suitable solvent or diluent, including condensed monomer, is used in said polymerization process. It is, however, preferred to form the catalyst in a separate step in a suitable solvent prior to adding the same to the polymerization step. While the catalysts do not contain pyrophoric species, the catalysts' components are sensitive to both moisture and oxygen and should be handled and transferred in an inert atmosphere such as nitrogen, argon or helium.

In preferred embodiments of the invention the transition metal compounds used to form the catalyst composition are of the formula

wherein:

Z is a group 3 to 10 transition metal, $X_1$ is an anionic leaving group ligand or a non-coordinating anion leaving group, $X_2$ is a hydride or hydrocarbyl ligand, and (LS) is a ligand system which completes the coordination number of Z.

Preferably, the transition metal compound has a ligand system (LS) coordinated to the transition metal which comprises (i) two cyclopentadienyl ligands, each optionally substituted and the two optionally being bridged with a bridging atom or group or (ii) a single, optionally substituted, cyclopentadienyl ligand and a heteroatom—containing ligand, the two ligands optionally being bridged with a bridging atom or group.

In particular it is preferred to use such transition metal compounds where each of $X_1$ and $X_2$ is independently an alkyl group such as methyl.

The preferred polyanionic activator composition has $(pfp)_3B$ non-coordinating anionic groups bonded to the core.

Reaction of the transition metal compound with the preferred activator composition therefore yields an active catalyst composition represented by the formula

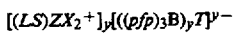

In the case where the balancing cation of the activator composition is a Bronsted acid $LH^+$, the Lewis base L liberated during catalyst formation either remains in solution or is weakly associated with the transition metal cation center. Ammonium cations are the preferred balancing cation component of the activator composition.

In summary, a polyanionic activator moiety may be prepared from an intermediate compound in which the metal or metalloid element of the NCA group is chemically bonded to a reactive functional group, said radical being chemically reactable with the core component, or being polymerizable with other intermediates compounds and optionally other comonomers to form the core component.

5. Polymerization Process

In general the improved catalyst of this invention will polymerize olefins, diolefins and/or acetylenically unsaturated monomers either alone or in combination with other olefins and/or other unsaturated monomers at conditions well known in the prior art for conventional Ziegler-Natta catalysis. The catalyst may be used to polymerize ethylene, α-olefins and/or acetylenically unsaturated monomers having from about 2 to about 18 carbon atoms and/or diolefins having from about 4 to about 18 carbon atoms either alone or in combination. The catalyst may also be used to polymerize ethylene, α-olefins, diolefins and/or acetylenically unsaturated monomers in combination with other unsaturated monomers.

In the polymerization process of this invention, the molecular weight appears to be a function of both polymerization temperature and pressure. The polymers produced with the catalyst of this invention, when prepared in the absence of significant mass transport effects, will, generally, have relatively narrow molecular weight distributions.

In general, catalysts can be selected so as to produce the polymer products which will be free of certain trace metals generally found in polymers produced with Ziegler-Natta type catalysts such as aluminum, magnesium, chloride and the like. The polymer products produced with the catalysts of this invention should, then, have a broader range of applications than polymers produced with more conventional Ziegler-Natta type catalysts comprising a metal alkyl, such as an aluminum alkyl.

In a preferred embodiment, the catalyst, immediately after formation, will then be used to homo- or copolymerize lower olefins particularly ethylene or propylene, at a temperature within the range from about 0° C. to about 100° C. and at a pressure within the range from about 15 to about 500 psig. In a most preferred embodiment of the present invention, the most preferred catalyst for the formation of ethylene based polymers will be used either to homopolymerize ethylene or to copolymerize ethylene with a lower α-olefin having from 3 to about 8 carbon atoms, thereby yielding a plastic or an elastomeric copolymer. In both the preferred and most preferred embodiments, the monomers will be maintained at polymerization conditions for a nominal holding time within the range from about 1 to about 60 minutes and the catalyst will be used at a metallocene concentration within the range from about $10^{-5}$ to about $10^{-1}$ moles per liter of diluent.

Polymerization may also occur with the inventive catalyst wherein the activated catalyst composition is immobilized with regard to a fluidized flow of monomer or polymer, which process comprises maintaining monomer in fluidized contact with the immobilized activated catalyst composition at a temperature and for a time sufficient to polymerize at least a portion of the olefin to a polyolefin, and removing the polyolefin from contact with the activated catalyst composition.

EXAMPLES

Having described the present invention broadly and with its preferred and most preferred embodiments, it is believed the same will become more apparent from the following illustrative, but not limiting examples.

All examples were completed under inert conditions substantially free of moisture using standard techniques such as Schlenk technique or conducted in a vacuum atmosphere dry box. Solvents and reagents were dried by standard techniques prior to use. The metallocenes used were either purchased or prepared in accordance with published techniques. Solid state $^{13}$C NMR spectroscopy and solution $^1$H NMR spectroscopy were employed to characterize the products.

EXAMPLE 1

In 100 mls of diethylether (Et$_2$O) containing 2.0 g of Mg metal shavings (pretreated with 1,2 dibromoethane to clean surface) 10.5 g of 2-bromomethy-5-norbornene was added dropwise at room temperature under rapid stirring. The formation of the Grignard reagent proceeded quickly to form a light amber solution. The solution was filtered to remove the excess Mg metal to yield 93 mls of Grignard reagent. Thereafter, 4.6 g of tripentafluoro-phenyl boron was added to 15 cc of the Grignard reagent in 50 ml of Et$_2$O. The mixture was stirred for 10 minutes at room temperature before pentane (50 ml) was added to precipitate a white ionic solid. The solid was collected by filtration, washed with pure pentane and dried in vacuum. The $^1$H NMR spectrum of the solid in d$_8$-THF was dominated by THF signals but a clean multiplet was observed at 6 ppm which are characteristic for the inequivalent olefinic protons on the norbornylene group (nb) of a composition Of the structure [MgBr THF$_x$]$^+$[(pfp)$_3$Bnb]$^-$. High field $^{13}$C NMR spectroscopy verified the structure.

EXAMPLE 2

5.28 g of the glassy white solid precipitate prepared in Example 1 was suspended in 100 mls of water at room temperature after which 1.15 g of dimethylanilinium hydrochloride was added to the solution and stirred for 10 minutes. The reaction mixture was transferred to a separatory funnel and was extracted with methylene chloride (2 times with 50 mls). The methylene chloride layers were combined and washed 3 times with 50 mls of water to remove excess dimethylanilinum hydrochloride. Thereafter the methylene chloride extracts were dried using Na$_2$SO$_4$, filtered. The product was crystallized from methylene chloride concentrates at low temperature to yield 2.9 grams of [DMAH]$^+$[(pfp)$_3$Bnb]$^-$.

EXAMPLE 3

1.0 g grams of [DMAH]$^+$[(pfp)$_3$Bnb]$^-$ prepared as in Example 2 was suspended in 25 mls of toluene to give a two phase liquid (top phase toluene rich, bottom phase boron reagent rich). 0.06 g of Cp$_2$HfMe$_2$ was added to the well stirred mixture at ambient temperature causing an immediate temperature increase of 1–2 degrees (23°–25° C.). After 30 minutes a yellow oil precipitated from solution. The oil was isolated, washed with pure toluene (three times with 20 mls), and dried to yield 0.8 grams of a glassy solid. The solid was dissolved in methylene chloride and washed three times with water to remove catalyst residue. The methylene chloride extract was dried over Na$_2$SO$_4$, after which the product was isolated by precipitation with excess pentane. The signals assigned to the two inequivalent olefinic protons on the starting synthon had disappeared indicating complete oligomerization of the synthon anion.

EXAMPLE 4

In 10 mls of tetrahydrofuran (THF) containing 1.3 g of Mg metal shavings (pretreated with 1,2 dibromoethane to clean surface) 2 g of 2-4-bromostyrene was added dropwise at 50° C. under rapid stirring. The formation of the Grignard reagent proceeded quickly to form a light amber solution. The solution was filtered to remove the excess Mg metal. Thereafter, 7.8 g of tripentafluorophenylboron in 25 mls THF was added to the Grignard reagent at room temperature. The mixture was stirred for 10 minutes at room temperature before pentane (50 ml) was added to precipitate a white ionic solid. The solid was collected by filtration, washed with pure pentane and dried in vacuum. The $^1$H and $^{13}$C NMR spectra of the solid in d$_8$-THF confirmed the structure to be the THF adduct of the magnesium bromide salt of the styrene (Sty) modified synthon: [MgBr THF$_x$]$^+$[(pfp)$_3$BSty]$^-$.

EXAMPLE 5

2.0 g of the styrene modified synthon prepared in Example 4 was dissolved in 50 mls of methylene chloride. The methylene chloride layer was treated with 0.3 grams of dimethylanilinium hydrochloride. The resulting mixture was washed three times with 50 mls of water to remove the magnesium halide biproduct. The methyene chloride layer was dried using Na$_2$SO$_4$, filtered. The product was crystallized from methylene chloride concentrates at low temperature to yield 0.7 grams of a thermally unstable white solid. The initially isolated material was characterized to be [DMAH]$^+$[(pfp)$_3$BSty]$^-$. Thermal decomposition via cationic mechanisms led to the oligomerization of the target synthon over 12 hours at room temperature. The isolated synthon and its' thermal decomposition products were reacted with Cp$_2$HfMe$_2$ and formed active olefin polymerization catalysts.

EXAMPLE 6

3.43 g of the product prepared in Example 4 was dissolved in 15 mls of methylene chloride and treated with 0.85 g of Et$_4$N$^+$Cl$^-$. Excess 1,4 dioxane was added to precipitate the magnesium halide. The insolubles were removed by filtration, and the resulting methylene chloride solution of the crude product was washed three times with water, dried over Na$_2$SO$_4$, and was crystallized by addition of Et$_2$O. The resulting thermally stable crystalline product was found to have the composition, [Et$_4$N]$^+$[(pfp)$_3$BSty]$^-$, by high field NMR spectroscopy.

EXAMPLE 7

0.26 grams of DVB (a mixture of divinylbenzene isomers) was dissolved in 50 mls of pentane. 1.5 mls of 1.3 M s-BuLi was added to the stirred solution causing an immediate color change from clear to orange. After 5 minutes a orange polymeric solid precipitate had formed and 1 g of tripentafluoro-phenylboron was added causing formation of a lightly color solid precipitate. The solvent was reduced by 30% and 0.28 grams of [DMAH][Cl] in 50 mls of methylene chloride was added. A white precipitate is formed. The precipitate was removed by filtration. The soluble portion was concentrated and titurated with excess pentane to precipitate a white polyionic solid. The solid was isolated by filtration, extracted with methylene chloride, filtered, and reprecipitated with pentane to give a low molecular weight polyionic activator: [DMAH$^+$]$_n$[((pfp)$_3$B)$_n$—PDVB]$^{n-}$ (where PDVB represents a polydivinylbenzene oligomeric core T).

EXAMPLE 8

5 grams of paramethylstyrene (PMS) and 0.5 g of DVB were diluted in 100 mls of pentane and stirred while 3.6 mls of a 1.09 M solution of s-BuLi was added. The formation of a red gel began to form indicating the formation of the desired living crosslinked poly-PMS core identified above as T''. The pentane was removed in vacuum and 3.97 grams of B(pfp)$_3$ in 50 mls of toluene was added. The mixture was stirred for 3 hours before the red color had disappeared leaving an off-white gel/toluene mixture. The solvent was removed in vacuum and 0.56 grams of [DMAH][C1] in 100 mls of methylene chloride was added. The mixture was stirred 12 hours, filtered. The solid was washed 3 times with 20 mls of methylene chloride, and dried in vacuum to give 4.8 grams of a crosslinked polystyrene supported polyionic activator: [DMAH$^+$]$_n$[((pfp)$_3$B)$_n$—XPMS]$^{n-}$ (where XPMS represents the crosslinked polyparamethylstyrene core identified above as T).

EXAMPLE 9

Bulk propylene (400mls) was polymerized in a stainless steel autoclave at 40° C. using a catalyst prepared by the combination of 0.022 g of rac-Me$_2$Si(H$_4$-Indenyl)ZrMe$_2$ and 0.007 g of the norbornylene functionalized synthon prepared in Example 2. The reactor temperature increased to 42° C. during the 30 minute polymerization. The unreacted propylene was vented and 28 grams of isotactic polypropylene was isolated. GPC established that the polymer had a weight average molecular weight of 17K and a molecular weight distribution of 2.4.

EXAMPLE 10

Bulk propylene (400mls) was polymerized in a stainless steel autoclave at 40° C. using a catalyst prepared by the combination of 0.018 g of rac-Me$_2$Si(H$_4$-Indenyl)ZrMe$_2$ and 0.006 g of the polynorbornylene polyionic activator prepared in Example 3. The reactor temperature increased to 45° C. during the 5 minute polymerization. The unreacted propylene was vented and 38 grams of isotactic polypropylene was isolated. GPC established that the polymer had a weight average molecular weight of 20K and a molecular weight distribution of 2.6.

EXAMPLE 11

Bulk propylene (400 mls) was polymerized in a stainless steel autoclave at 40° C. using a catalyst prepared by the combination of 0.019 g of rac-Me$_2$Si(H$_4$-Indenyl)ZrMe$_2$ and 0.006 g of the DVB polyionic activator prepared in Example 7. The reactor temperature was held at 40° C. during the 30 minute polymerization. The unreacted propylene was vented and 4.1 grams of isotactic polypropylene was isolated. GPC established that the polymer had a weight average molecular weight of 10K and a molecular weight distribution of 2.5.

EXAMPLE 12

Bulk propylene (400 mls) was polymerized in a stainless steel autoclave at 40° C. using a catalyst prepared by the combination of 0.10 g of rac-Me$_2$Si(H$_4$-Indenyl)ZrMe$_2$ and 0.10 g of the Styrene-DVB polyionic activator prepared in Example 8. The reactor temperature increased to 48° C. during the 30 minute polymerization. The unreacted propylene was vented and 150 grams of granular isotactic polypropylene was isolated. GPC established that the had a weight average molecular weight of 23K and a molecular weight distribution of 2.2.

Although the invention has been described with reference to its preferred embodiments those skilled in the art may appreciate changes and modification thereto which do not depart from the scope and spirit of the invention as described above and claimed hereafter.

I claim:

1. A polyanionic moiety comprising a plurality of metal or metalloid atom-containing non coordinating anionic groups pendant from and chemically bonded to a core component, wherein the anionic groups are represented by the formula $$(Q_1Q_2 \ldots Q_n MD_d)^-$$

wherein:

M is a metal or metalloid element selected from Groups 3–15;

$Q_1-Q_n$ are radical ligands each of which is, independently, hydride, halide, disubstituted amido, alkoxide, aryloxide, hydrocarbyl, substituted hydrocarbyl, halocarbyl, substituted halocarbyl, or a hydrocarbyl-or halocarbyl-substituted organometalloid;

n is the number of Q-ligands;

d is 0 or 1; and when d is 1, D is a bridging moiety which links a pendant non-coordinating anion to the core.

2. The polyanionic moeity according to claim 1 wherein the bridging moiety is a hydrocarbyl, halocarbyl, substituted hydrocarbyl, hydrocarbyloxy, aryloxy, oxo, imido, or sulfido group.

3. The moeity polyanionic according to claim 2 wherein the bridging moiety is represented by the following:

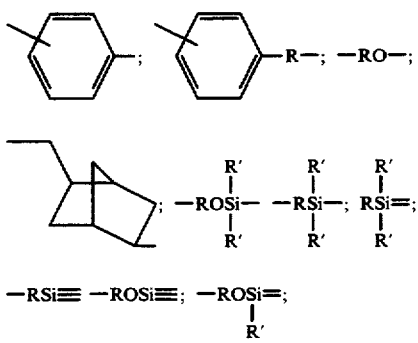

wherein R is a hydrocarbyl radical.

4. The polyanionic moeity of claim 1 wherein, at least one of said radical ligands is an aromatic or substituted aromatic radical containing from 6–20 carbon atoms.

5. The polyanionic moeity of claim 4 wherein at least one radical ligand is a pentafluorophenyl group.

6. The polyanionic moeity of claim 1 wherein the metal or metalloid is an element of Group 4, 5 or 13.

7. The polyanionic moeity of claim 6 wherein the metal or metalloid is boron or aluminum.

8. The polyanionic moeity of claim 7 represented by the formula $$[(ArAr'Q_1BD_d)_y(T)]^{-Y}$$

wherein

Ar and Ar' are the same or different aromatic or substituted aromatic hydrocarbyl radical containing from 6 to 20 carbon atoms;

T is the core component;

B is boron;

d is 0 or 1;

when d is 1, D is a bridging moiety which links the boron atoms to the core T;

$Q_1$ is a halide, hydride, hydrocarbyl or substituted hydrocarbyl radical containing from 1 to 20 carbon atoms, or an aromatic or substituted aromatic radical containing at least 6 carbon atoms; and y is an integer equal to or greater than 2.

9. The polyanionic moeity of claim 8 represented by the formula $$[((pfp)_3B-D_d)_y(T)]^{-Y}$$

wherein pfp is pentafluorophenyl.

10. The polyanionic moeity of claim 9 wherein T is selected from one of cross-linked polystyrene, polydivinyl benzene, or metal oxides.

11. A composition comprising a polyanionic moeity according to claim 1 and a plurality of cations Ct which balance the charge of the anionic groups.

12. A catalyst precursor composition represented by the formula:

wherein

T is a core component;

Ct is a counter cation;

c+ represents the charge of Ct

NCA is a non-coordinating anion pendant from core T;

y is a number greater than 1 representing the number of pendant NCA groups;

b is the charge on the NCA; and y' is the number of Ct cations such that y' times c+ equals y times b.

13. The composition of claim 12 wherein NCA is represented by the formula $$(Q_1Q_2 \ldots Q_nMD_d)^{b-}$$

wherein

M is a metal or metalloid element selected from Groups 3–15;

$Q_1$–$Q_n$ are radical ligands selected from the group of hydride, halide disubstituted amido, alkoxide, aryloxide, hydrocarbyl, substituted hydrocarbyl, halocarbyl, substituted halocarbyl, or hydrocarbyl-or halocarbyl-substituted organometalloid radicals;

n is the number of Q-ligands;

d is 0 or 1;

when d is 1, D is a bridging moiety which links the pendant NCA to the core.

14. The composition of claim 12 wherein Ct is a cation reactive with a leaving group ligand of a ligand stabilized transition metal compound.

15. The composition of claim 14 wherein Ct is represented by the formula $$[LH]^+$$

wherein

L is a neutral Lewis base and $[LH]^+$ is a Bronsted acid.

16. A composition represented by the formula

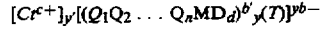

wherein:

Ct is a counter cation capable of reacting with a transition metal alkyl complex;

M is a metal or metalloid selected from Groups 3–15;

$Q_1$–$Q_n$ are, independently, hydride radicals, halide radicals, disubstituted amido radicals, alkoxide radicals, aryloxide radicals, hydrocarbyl radicals, substituted hydrocarbyl radicals, halocarbyl radicals, substituted halocarbyl radicals, hydrocarbyl- and halocarbyl-substituted organometalloid radicals;

n is the number of Q ligands bonded to M;

d is 0 or 1 and when d is 1, D is a hydrocarbyl, halocarbyl, substituted hydrocarbyl, hydrocarbyloxy or aryloxy, oxo, imido, or sulfido bridging group;

T is an core moiety chemically bonded to each M or D;

y is greater than one and represents the number of M-containing anionic groups pendant from T; b is the charge on the anionic pendant groups; c+ is the charge on the counter cation c+; and y' times c+ equals y times b.

17. The composition of claim 16 wherein T is cross-linked polystyrene or polydivinyl benzene.

18. The composition of claim 16 wherein T is silica or a metal oxide.

19. The composition of claim 16 wherein [Ct] is a Bronsted acid represented by the formula $$[LH]^+$$

wherein
L is a neutral Lewis base.

20. A catalyst composition comprising the polyanionic moiety of claim 1 and sufficient cations to balance charge on the composition.

21. A catalyst composition represented by the formula $$[(LS)ZX_2{}^{n+}]_y[(NCA^{b-})_yT]^{yb-}$$

wherein
Z is a group 3 to 10 transition metal;
X is a hydride or hydrocarbyl ligand;
(LS) is a ligand system which completes the coordination number of Z;
NCA is a non-coordinating anion bonded to core T;
y is a number greater than 1 representing 'the number of pendant NCA groups;
b is the charge on the NCA; and
y' is the number of catalyst cations such that y' times c+ equals y times b and n is the charge on the catalyst cations.

22. The composition of claim 21 wherein the ligand system (LS) comprises two substituted or unsubstituted cyclopentadienyl ligands, optionally bridged with a bridging atom or group.

23. The composition of claim 21 wherein the ligand system (LS) comprises a single, substituted or unsubstituted cyclopentadienyl ligand and a heteroatom containing ligand, optionally bridged with a bridging atom or group.

24. The composition of claim 21 wherein $[NCA^{b-})_yT]^{yb-}$ is $[((pfp)_3BD_d)_y(T)]^{-Y}$
wherein
pfp is pentafluorophenyl;
B is boron;
d is 0 or 1;
when d is 1, D is a bridging moiety which links the boron atoms to the core T; and
y is an integer equal to or greater than 2.

25. A method of preparing a catalyst, comprising the steps of combining;
(a) at least one transition metal compound having at least one leaving group ligand; and,
(b) an activator composition comprising a core having a plurality of pendent non-coordinating anion groups the charge of which are balanced to neutral by cationic groups which are reactable with the leaving group ligand of the transition metal compound.

26. A method of preparing a catalyst precursor composition comprising the step of contacting a compound represented by the formula $$[Ct^+]_y[Q_1Q_2\ldots Q_nMD']^{b-}$$

wherein:
Ct is a counter cation capable of reacting with a transition metal alkyl complex;
M is a metal or metalloid selected from Groups 3–15;
$Q_1$–$Q_n$ are, independently, hydride radicals, halide radicals, disubstituted amido radicals, alkoxide radicals, aryloxide radicals, hydrocarbyl radicals, substituted hydrocarbyl radicals, halocarbyl radicals, substituted halocarbyl radicals, hydrocarbyl- and halocarbyl-substituted organometalloid radicals;
n is the number of Q ligands bonded to M;
D' is a radical group containing at least one functional group;
y' is the number of Ct cations;
y' times c+ equals b−;
with a coupling agent polymerization initiator and a substrate, T', wherein T' has at least one functional group reactable with D', under conditions suitable to cause reaction of the D' functional group with T'.

27. A method of preparing a polyanionic activator compound comprising the step of contacting a compound represented by the formula:

$$[Q_1Q_2\ldots Q_nM]$$

wherein:
M is a metal or metalloid selected from Groups 3–15;
$Q_1$–$Q_n$ are independently, hydride radicals, halide radicals, disubstituted amido radicals, alkoxide radicals, aryloxide radicals, hydrocarbyl radicals, substituted hydrocarbyl radicals, halocarbyl radicals, substituted halocarbyl radicals, hydrocarbyl and halocarbyl-substituted organometalloid radicals;
n is the number of Q ligands bonded to M;
with a polyionic preformed core represented by the general formula:

$$[Ct^+]_y[T']^{y-}$$

wherein:
Ct is a counter cation capable of reacting with a transition metal alkyl complex;
T" is a polyaniorfic Lewis basic core substrate and y' times c+ equals y−;
to form a product represented by the general formula:

$$[Ct^+]_y[(Q_1Q_2\ldots Q_nM)_uT']^{y-}.$$

* * * * *